(12) United States Patent
Maillet

(10) Patent No.: US 11,077,118 B2
(45) Date of Patent: Aug. 3, 2021

(54) METHODS AND COMPOSITIONS FOR IBOGAINE TREATMENT OF IMPULSE CONTROL DISORDER, ANXIETY-RELATED DISORDERS, VIOLENCE AND/OR ANGER, OR REGULATING FOOD INTAKE

(71) Applicant: DemeRx, Inc., Miami, FL (US)

(72) Inventor: Emeline Maillet, New Orleans, LA (US)

(73) Assignee: DEMERX, INC., Miami, FL (US)

( * ) Notice: Subject to any disclaimer, the term of this patent is extended or adjusted under 35 U.S.C. 154(b) by 0 days.

(21) Appl. No.: 15/454,305

(22) Filed: Mar. 9, 2017

(65) Prior Publication Data

US 2020/0093833 A1 Mar. 26, 2020

Related U.S. Application Data

(63) Continuation of application No. 14/635,905, filed on Mar. 2, 2015, now Pat. No. 9,592,239.

(60) Provisional application No. 62/049,968, filed on Sep. 12, 2014.

(51) Int. Cl.
A61K 31/55 (2006.01)
A61K 31/00 (2006.01)

(52) U.S. Cl.
CPC .............. *A61K 31/55* (2013.01); *A61K 31/00* (2013.01)

(58) Field of Classification Search
CPC ........ A61K 31/55; C07D 471/22; A61P 25/00
USPC ..................................... 514/214.02; 540/579
See application file for complete search history.

(56) References Cited

U.S. PATENT DOCUMENTS

| | | | |
|---|---|---|---|
| 2,817,623 | A | 12/1957 | Schneider |
| 3,715,361 | A | 2/1973 | Epstein et al. |
| 4,499,096 | A | 2/1985 | Lotsof |
| 4,626,539 | A | 12/1986 | Aungst et al. |
| 4,806,341 | A | 2/1989 | Chien et al. |
| 4,857,523 | A | 8/1989 | Lotsof |
| 5,026,697 | A | 6/1991 | Lotsof |
| 5,149,538 | A | 9/1992 | Granger et al. |
| 5,152,994 | A | 10/1992 | Lotsof |
| 5,616,575 | A | 4/1997 | Efange et al. |
| 5,925,634 | A | 7/1999 | Olney |
| 7,638,651 | B2 | 12/2009 | Gant et al. |
| 8,362,007 | B1 | 1/2013 | Mash et al. |
| 8,367,693 | B1 | 2/2013 | King et al. |
| 8,741,891 | B1 | 6/2014 | Mash |
| 2003/0153552 | A1 | 8/2003 | Mash et al. |
| 2003/0199439 | A1 | 10/2003 | Simon |
| 2005/0022270 | A1 | 1/2005 | Hildebrand et al. |
| 2005/0148673 | A1 | 7/2005 | Harbut et al. |
| 2005/0203011 | A1 | 9/2005 | Ron |
| 2005/0222270 | A1 | 10/2005 | Olney et al. |
| 2006/0128610 | A1 | 6/2006 | Cooper |
| 2007/0185085 | A1 | 8/2007 | Mash |
| 2008/0234257 | A1 | 9/2008 | Gant et al. |
| 2008/0280886 | A1 | 11/2008 | Gant et al. |
| 2009/0082388 | A1 | 3/2009 | Hacksell et al. |
| 2009/0098069 | A1 | 4/2009 | Vacca |
| 2009/0252786 | A1 | 10/2009 | Hanz |
| 2009/0258869 | A1 | 10/2009 | Ron et al. |
| 2010/0311722 | A1 | 12/2010 | Mash |
| 2010/0311723 | A1 | 12/2010 | Mash |
| 2010/0311724 | A1 | 12/2010 | Mash |
| 2010/0311725 | A1 | 12/2010 | Mash |
| 2012/0083485 | A1 | 4/2012 | Mash |
| 2014/0288056 | A1 | 9/2014 | Friedhoff |
| 2015/0045350 | A1 | 2/2015 | Friedhoff |
| 2015/0231145 | A1 | 8/2015 | Friedhoff |
| 2015/0231146 | A1 | 8/2015 | Friedhoff |
| 2015/0231147 | A1 | 8/2015 | Friedhoff |
| 2015/0238503 | A1 | 8/2015 | Maillet et al. |
| 2015/0246055 | A1 | 9/2015 | Friedhoff |
| 2015/0257667 | A1 | 9/2015 | Friedhoff |
| 2015/0258104 | A1 | 9/2015 | Friedhoff |
| 2015/0258105 | A1 | 9/2015 | Maillet et al. |
| 2015/0258106 | A1 | 9/2015 | Friedhoff |
| 2015/0258107 | A1 | 9/2015 | Friedhoff |
| 2015/0258109 | A1 | 9/2015 | Maillet et al. |
| 2015/0258110 | A1 | 9/2015 | Maillet et al. |
| 2015/0258111 | A1 | 9/2015 | Maillet et al. |
| 2015/0258112 | A1 | 9/2015 | Friedhoff |
| 2015/0258113 | A1 | 9/2015 | Friedhoff |
| 2015/0258114 | A1 | 9/2015 | Friedhoff |

(Continued)

FOREIGN PATENT DOCUMENTS

| | | |
|---|---|---|
| BE | 664377 A | 9/1965 |
| BE | 806438 A | 2/1974 |

(Continued)

OTHER PUBLICATIONS

Alper, K. R. et al., 'Treatment of acute opioid withdrawal with ibogaine', The American Journal on Addictions, 1999, vol. 8, No. 3, pp. 234-242. See abstract: and pp. 237 and 238.
Buchi et al. "Chemical Transformations of Ibogaine," Journal of the American Chemical Society, vol. 88, Jun. 5, 1966, pp. 2532-2535.
Buchi et al., "The Total Synthesis of Iboga Alkaloids," J. Am. Chem Society, 1966, 88 (13) pp. 3099-3109.
Buchi et al., The Total Synthesis of Iboga Alkaloids, 1996, J Am Chem Society, Jul. 5, 1996, 88:13, pp. 3099-3109.
Fermini et al. Nature Reviews Drug Discovery 2003, 2, pp. 439-447.
Hoelen et al., Long-QT Syndrome Induced by the Antiaddiction Drug Ibogaine, Jan. 15, 2009, N Engl J Med, 360(3) pp. 308-309.
ISR and Written Opinion issued on PCT/US2015/018356, dated May 20, 2015.

(Continued)

*Primary Examiner* — Jeffrey H Murray
(74) *Attorney, Agent, or Firm* — Cooley LLP

(57) ABSTRACT

This invention provides a method for treating anxiety-related disorder or impulse control disorder, regulating food intake, attenuating food cravings, or treating anger and/or violence and disorders associated therewith in a patient, comprising administering to the patient in need thereof a therapeutically effective amount of ibogaine, ibogaine derivative, or a pharmaceutically acceptable salt and/or solvate thereof.

14 Claims, No Drawings

(56) References Cited

U.S. PATENT DOCUMENTS

| | | |
|---|---|---|
| 2015/0342959 A1 | 12/2015 | Friedhoff |
| 2016/0008372 A1 | 1/2016 | Weis |
| 2016/0038505 A1 | 2/2016 | Maillet et al. |
| 2016/0074414 A1 | 3/2016 | Maillet |
| 2016/0220579 A1 | 8/2016 | Weis et al. |
| 2016/0271139 A1 | 9/2016 | Friedhoff |
| 2017/0354662 A1 | 12/2017 | Weis |
| 2017/0368073 A1 | 12/2017 | Friedhoff |
| 2017/0368074 A1 | 12/2017 | Maillet et al. |
| 2018/0280406 A1 | 10/2018 | Friedhoff |
| 2020/0078367 A1 | 3/2020 | Friedhoff |
| 2020/0085836 A1 | 3/2020 | Maillet et al. |

FOREIGN PATENT DOCUMENTS

| | | | |
|---|---|---|---|
| DE | 19 02 227 A1 | 9/1969 | |
| DE | 24 10 651 A1 | 9/1974 | |
| DE | 24 50 188 A1 | 5/1975 | |
| DE | 20 2008 007 923 U1 | 9/2008 | |
| WO | WO-91/18609 A1 | 12/1991 | |
| WO | WO-97/29735 A1 | 8/1997 | |
| WO | WO-00/17366 A2 | 3/2000 | |
| WO | WO-01/52851 A1 | 7/2001 | |
| WO | WO-03/066029 A2 | 8/2003 | |
| WO | WO-03/066030 A2 | 8/2003 | |
| WO | WO-2005/079767 A2 | 9/2005 | |
| WO | WO-2008/039179 A1 | 4/2008 | |
| WO | WO-2012/019106 A2 | 2/2012 | |
| WO | WO-2013/063673 A1 | 5/2013 | |
| WO | WO-2015/134405 A1 | 9/2015 | |
| WO | WO2015/163844 | * 10/2015 | ........... C07D 487/04 |
| WO | WO-2015/163844 A1 | 10/2015 | |

OTHER PUBLICATIONS

Krantz et al. Annals of Internal Medicine, vol. 150, pp. 387-395, publ. 2009.

Lotsof and Wachtel, Manual for Ibogaine Therapy: Screening, Safety, Monitoring & Aftercare, 2d revision, 2003, www.ibogainedeskl.nl/manual.html.

Malik et al. Evaluation of drug-induced QT interval prolongation: implications for drug approval and labelling. Drug Safety, Adis International Ltd., vol. 24(5), pp. 323-351 (2001).

Rezvani, A. H. et al. "Attenuation of alcohol intake by ibogaine in three strains of alcohol-preferring rats," Pharmacology Biochemistry and Behavior, 1995, vol. 52, No. 3, pp. 615-620. See abstract: and pp. 615 and 616.

* cited by examiner

METHODS AND COMPOSITIONS FOR IBOGAINE TREATMENT OF IMPULSE CONTROL DISORDER, ANXIETY-RELATED DISORDERS, VIOLENCE AND/OR ANGER, OR REGULATING FOOD INTAKE

CROSS-REFERENCE TO RELATED APPLICATIONS

This application is a continuation of U.S. Non-Provisional patent application Ser. No. 14/635,905, filed Mar. 2, 2015, which claims benefit from U.S. Provisional Application No. 62/049,968, filed Sep. 12, 2014, which is hereby incorporated by reference in its entirety.

FIELD OF THE INVENTION

This invention relates generally to methods for the treatment of anxiety-related disorders, including obsessive-compulsive disorder (OCD), or impulse control disorder by administering ibogaine, an ibogaine derivative, or a pharmaceutically acceptable salt and/or solvate thereof (hereinafter referred to as "ibogaine"). This invention further relates generally to methods and compositions for the regulation of food intake by administering ibogaine, an ibogaine derivative, or a pharmaceutically acceptable salt thereof. This invention further relates generally to methods and compositions for treating anger and/or violence and disorders associated therewith by administering ibogaine, an ibogaine derivative, or a pharmaceutically acceptable salt thereof.

STATE OF THE ART

Obsessive compulsive disorder is characterized by recurrent and persistent ideas, thoughts, impulses or images (obsessions) that are ego-dystonic and/or repetitive, purposeful and intentional behaviors (compulsions) that are recognized by the person as excessive or unreasonable (American Psychiatric Association, 1994a). The obsessions or compulsions cause marked distress, are time-consuming, and/or significantly interfere with social or occupational functioning.

Panic disorder is characterized by recurrent unexpected panic attacks and associated concern about having additional panic attacks, worry about the implications or consequences of the attacks, and/or a significant change in behavior related to the attacks (American Psychiatric Association, 1994a). A panic attack is defined as a discrete period of intense fear or discomfort in which four (or more) of the following symptoms develop abruptly and reach a peak within 10 minutes: (1) palpitations, pounding heart, or accelerated heart rate; (2) sweating; (3) trembling or shaking; (4) sensations of shortness of breath or smothering; (5) feeling of choking; (6) chest pain or discomfort; (7) nausea or abdominal distress; (8) feeling dizzy, unsteady, lightheaded, or faint; (9) derealization (feelings of unreality) or depersonalization (being detached from oneself); fear of losing control; (11) fear of dying; (12) paresthesias (numbness or tingling sensations); (13) chills or hot flushes. Panic disorder may or may not be associated with agoraphobia, or an irrational and often disabling fear of being out in public.

Social anxiety disorder, also known as social phobia, is characterized by a marked and persistent fear of one or more social or performance situations in which the person is exposed to unfamiliar people or to possible scrutiny by others (American Psychiatric Association, 1994a). Exposure to the feared situation almost invariably provokes anxiety, which may approach the intensity of a panic attack. The feared situations are avoided or endured with intense anxiety or distress. The avoidance, anxious anticipation, or distress in the feared situation(s) interferes significantly with the person's normal routine, occupational or academic functioning, or social activities or relationships, or there is marked distress about having the phobias. Lesser degrees of performance anxiety or shyness generally do not require psychopharmacological treatment.

Generalized anxiety disorder is characterized by excessive anxiety and worry (apprehensive expectation) that is persistent for at least 6 months and which the person finds difficult to control (American Psychiatric Association, 1994a). It must be associated with at least 3 of the following 6 symptoms: restlessness or feeling keyed up or on edge, being easily fatigued, difficulty concentrating or mind going blank, irritability, muscle tension, and sleep disturbance. The diagnostic criteria for this disorder are described in further detail in DSM-IV, which is incorporated herein by reference (American Psychiatric Association, 1994a).

Impulse control disorder is a class of psychiatric disorders involving the failure to resist a temptation, urge, or impulse (impulsivity) where such impulse is potentially harmful to the patient and/or others. The American Psychiatric Association's DSM-5 (May 2013) includes impulse control disorders "characterized by problems in emotional and behavioral self-control". These include borderline personality disorder, conduct disorder, antisocial personality disorder, attention deficit hyperactivity disorder (ADHD), schizophrenia, mood disorders, pathological gambling, pyromania, intermittent explosive disorder, kleptomania, sexual compulsion, paraphilia, internet addiction, trichotillomania, pathological skin picking, and compulsive shopping. Impulse control disorder may be related to anxiety disorder and/or OCD.

Violence and anger, particularly when out of proportion to a stimulus and/or a result of pathological anger, are associated with a number of mental disorders. These include oppositional defiant disorder, attention-deficit/hyperactivity disorder and conduct disorder (in children and adolescents), psychotic disorder, bipolar disorder, antisocial, borderline, paranoid and narcissistic personality disorders, adjustment disorder with disturbance of conduct, and intermittent explosive disorder. Pathological anger and violence account for a significant portion of violent crimes, including many high-profile crimes involving multiple victims. Highly volatile individuals are over-represented in the prison system in the United States.

Over ⅔ of adults in the U.S. are overweight, with about half of those being obese. The U.S. weight loss market is estimated to be worth over $60 billion; diet pills alone account for around $1 billion. However, many diet pills contain ingredients that are at best of dubious efficacy and at worst dangerous. Obesity greatly increases a person's risk for a variety of diseases, including coronary heart disease, high blood pressure, stroke, type 2 diabetes, abnormal levels of blood fats, metabolic syndrome, cancer, osteoarthritis, sleep apnea, reproductive issues, and gallstones.

Given the prevalence and impact of anxiety disorders, impulse control disorder, anger/violence-related disorders, and overweight/obesity, there is a need for treatments that address these issues. Prior to the embodiments described herein, the therapeutic dosing of ibogaine and its derivatives for treating anxiety disorders, impulse control disorder, anger/violence-related disorders, or regulation of food intake in humans at an acceptable QT interval prolongation has not previously been addressed, especially as it relates to dosing protocols that are effective, as well as safe.

SUMMARY OF THE INVENTION

Ibogaine has been used as a botanical preparation from the root bark of iboga tabernathe for over 100 years both as a crude preparation and as semisynthetic ibogaine, which was marketed in France until about 1970. In the United States, ibogaine is classified as a Schedule I controlled substance. The use of ibogaine in humans is complicated by the fact that the ranges in the prior art are exceptionally broad (0.01 to 1000 mg/kg body weight). Furthermore, the ranges generally used to treat addiction (e.g., 15 mg/kg to 20 mg/kg) cause hallucinations and may be fatal. Lotsof and Wachtel, Manual for Ibogaine Therapy: Screening, Safety, Monitoring & Aftercare (2d revision, 2003), accessed at www.ibogaine.desk.nl/manual.html; Hoelen, et al. New Engl. J. Med. 360(3), 308 (2009), which is incorporated herein by reference in its entirety for all of its methods, compositions and teachings.

A prolonged QT interval is a marker of potential ventricular tachyarrhythmia which can result in death. Serious complications, including ventricular tachyarrhythmia and death, can result from prolongation of the treated patient's QT interval by ibogaine, rendering high doses of ibogaine unacceptable. Heretofore, it was unclear whether a therapeutic dose of ibogaine could be found that resulted in QT interval prolongation within an acceptable range. It is expected that other compounds that share ibogaine's core structure will have a similar prolongation effect on QT interval. See, U.S. patent application Ser. No. 14/292,632 filed May 30, 2014 entitled METHOD FOR ACUTE AND LONG-TERM TREATMENT OF DRUG ADDICTION, which application is incorporated by reference in its entirety.

The current invention is predicated on the surprising discovery that treatment with a narrow dosage range of ibogaine or pharmaceutically acceptable salt and/or solvate thereof, between greater than about 1 mg/kg body weight and about 4 mg/kg body weight, provides a therapeutic reduction in symptoms of anxiety disorders, impulse control disorder, anger/violence-related disorders in affected patients, or provides a therapeutic reduction in food consumption. Preferably, the dose range that provides both therapeutic results and an acceptable QT interval prolongation of less than about 50 milliseconds is between about 1.3 mg per kg body weight and no more than about 4 mg per kg body weight and, more preferably between about 1 mg per kg body weight and no more than about 3 mg per kg body weight, or any subrange or subvalue within the aforementioned ranges.

In some embodiments, the dose that provides both therapeutic results and an acceptable QT interval prolongation of less than about 50 milliseconds is between about 60 mg and about 150 mg. In some embodiments, the dose that provides both therapeutic results and an acceptable QT interval prolongation of less than about 50 milliseconds is about 100 mg. In some embodiments, the dose that provides both therapeutic results and an acceptable QT interval prolongation of less than about 50 milliseconds is about 120 mg. In some embodiments, the dose that provides both therapeutic results and an acceptable QT interval prolongation of less than about 50 milliseconds is about 1.5 mg/kg body weight. In some embodiments, the dose that provides both therapeutic results and an acceptable QT interval prolongation of less than about 50 milliseconds is about 2 mg/kg body weight.

In some embodiments, the patient is administered an initial dose of ibogaine, ibogaine derivative, or pharmaceutically acceptable salt or solvate thereof, followed by one or more additional doses. In one embodiment, the initial dose is from about 50 mg to about 120 mg. In one embodiment, the one or more additional doses are lower than the initial dose. In one embodiment, the one or more additional doses are from about 5 mg to about 50 mg. In one embodiment, such a dosing regimen provides an average serum concentration of ibogaine of about 50 ng/mL to about 180 ng/mL. In one embodiment, the one or more additional doses maintain an average serum concentration of about 50 ng/mL to about 180 ng/mL over a period of time. In one embodiment, the one or more additional doses are administered periodically.

Furthermore, at very low doses, direct blood stream delivery of ibogaine may reduce symptoms of anxiety disorders, impulse control disorder, anger/violence-related disorders, or provide regulation of food intake. Such dosing is well below that previously described. Direct blood stream delivery of ibogaine enhances the amount of ibogaine delivered to the brain, because ibogaine does not pass through the liver as it does when ingested. Direct blood stream delivery of ibogaine includes sublingual, pulmonary and intranasal delivery where the ibogaine is absorbed directly into the blood stream and then into the brain. The rapid delivery of ibogaine into the brain, e.g. less than about 15 minutes, may cause a significant reduction in symptoms of anxiety disorders, impulse control disorder, anger/violence-related disorders, or food cravings.

In one aspect, this invention relates to treating anxiety disorders, impulse control disorder, anger/violence-related disorders, or regulation of food intake in a patient in need thereof comprising administering to the patient a therapeutically effective amount of ibogaine, ibogaine derivative, solvate, or pharmaceutically acceptable salt and/or solvate thereof. In one embodiment, this invention treats an anxiety disorder. In one embodiment, this invention treats OCD. In one embodiment, this invention treats generalized anxiety disorder. In one embodiment, this invention treats social anxiety disorder. In one embodiment, this invention treats panic disorder. In another embodiment, this invention treats impulse control disorder. In another embodiment, this invention treats pathological anger and/or violence. In another embodiment, this invention treats anger/violence-related disorders. In another embodiment, this invention reduces pathological anger in a patient. In another embodiment, this invention reduces violent outbursts in a patient. In another embodiment, this invention regulates food intake. In one embodiment, food consumption is reduced. In one embodiment, food cravings are reduced. In a preferred embodiment, the patient is not addicted to cocaine or an opiate.

In some embodiments, the therapeutic dose of ibogaine or pharmaceutically acceptable salt and/or solvate thereof administered to the patient is sufficient to provide a serum concentration of about 1000 to about 6000 ng·hour/mL (area under the curve for 24 hours). In some embodiments the therapeutic dose of ibogaine, ibogaine derivative, or pharmaceutically acceptable salt or solvate thereof administered to the patient is sufficient to provide a maximum serum concentration (Cmax) of less than about 250 ng/mL. In a preferred embodiment, the therapeutic dose provides a Cmax of about 100 ng/mL to about 200 ng/mL.

In some embodiments, the therapeutic dose of ibogaine, ibogaine derivative, or pharmaceutically acceptable salt or solvate thereof administered to the patient is sufficient to provide an average serum concentration of about 50 ng/mL to about 180 ng/mL, or any subrange or subvalue therebetween. In a preferred embodiment, the dose of ibogaine or pharmaceutically acceptable salt and/or solvate thereof administered to the patient provides an average serum concentration of about 50 ng/mL to about 110 ng/mL. In one embodiment, the dose of ibogaine or pharmaceutically acceptable salt and/or solvate thereof administered to the patient provides an average serum concentration of about 50 ng/mL to about 100 ng/mL. In one embodiment, the dose of ibogaine or pharmaceutically acceptable salt and/or solvate thereof administered to the patient provides an average serum concentration of less than about 50 ng/mL.

In a preferred embodiment, the narrow therapeutic doses of ibogaine, ibogaine derivative, or pharmaceutically acceptable salt and/or solvate thereof described above unexpectedly do not prolong the QT interval to unacceptable levels in human patients. In some embodiments, the patient will be pre-screened to evaluate tolerance for prolongation of QT interval, e.g., to determine whether the patient has any pre-existing cardiac conditions which would disqualify him/her from treatment with ibogaine or ibogaine derivative.

In some embodiments, the serum concentration is sufficient to inhibit or ameliorate symptoms of anxiety disorders, impulse control disorder, anger/violence-related disorders, or to regulate food intake while maintaining a QT interval of less than about 500 milliseconds (ms) during said treatment. In some embodiments, the dose of ibogaine or pharmaceutically acceptable salt and/or solvate thereof maintains a QT interval of less than about 450 ms. In some embodiments, the dose of ibogaine or pharmaceutically acceptable salt and/or solvate thereof maintains a QT interval of less than about 420 ms.

In some embodiments, the dose of ibogaine or pharmaceutically acceptable salt and/or solvate thereof provides prolongation of the QT interval of less than about 50 ms. In some embodiments, the dose of ibogaine or pharmaceutically acceptable salt and/or solvate thereof provides prolongation of the QT interval of less than about 30 ms. In a preferred embodiment, the dose of ibogaine or pharmaceutically acceptable salt and/or solvate thereof provides prolongation of the QT interval of less than about 20 ms. In a preferred embodiment, the patient is tested to determine QT interval before treatment with ibogaine, and if clinician determines that the QT prolongation would be an unacceptable risk, ibogaine therapy will be contraindicated.

In another aspect, this invention provides a method for treating anxiety disorders, impulse control disorder, anger/violence-related disorders, or regulating food intake in a patient in need thereof comprising administering to the patient ibogaine or an ibogaine derivative in a sustained release manner such that the concentration of ibogaine, ibogaine derivative, pharmaceutically acceptable salt and/or solvate thereof is maintained at a therapeutically effective amount for period of about 6 hours, about 12 hours, about 18 hours, about 24 hours, about 36 hours, about 48 hours, about 72 hours, about 96 hours, or a period of time between any two of these durations. In one embodiment, the average serum concentration is maintained at a therapeutically effective level for several days, weeks, months, or a year or more.

In some embodiments, the maintenance dose of ibogaine is 5 mg to 100 mg. In some embodiments, the maintenance dose of ibogaine is about 1.5 mg/kg body weight. In some embodiments, the maintenance dose of ibogaine is about 1 mg/kg body weight. In some embodiments, the maintenance dose of ibogaine is about 0.9 mg/kg body weight. In some embodiments, the maintenance dose of ibogaine is about 0.8 mg/kg body weight. In some embodiments, the maintenance dose of ibogaine is about 0.7 mg/kg body weight. In some embodiments, the maintenance dose of ibogaine is about 0.6 mg/kg body weight. In some embodiments, the maintenance dose of ibogaine is about 0.5 mg/kg body weight. In some embodiments, the maintenance dose of ibogaine is about 0.4 mg/kg body weight. In some embodiments, the maintenance dose of ibogaine is about 0.3 mg/kg body weight. In some embodiments, the maintenance dose of ibogaine is about 0.2 mg/kg body weight. In some embodiments, the maintenance dose of ibogaine is about 0.1 mg/kg body weight.

DETAILED DESCRIPTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

Definitions

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%.

"Administration" refers to introducing an agent into a patient. Typically, an effective amount is administered, which amount can be determined by the treating physician or the like. Any route of administration, such as topical, subcutaneous, peritoneal, intraarterial, inhalation, vaginal, rectal, nasal, buccal, introduction into the cerebrospinal fluid, or instillation into body compartments can be used. The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of ibogaine, ibogaine derivative, or salt and/or solvate thereof one, two, three, or more times per day. Administration may be via transdermal patch, gum, lozenge, sublingual tablet, intranasal, buccal, intrapulmonary, oral administration, or any other mode of administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, 
is a single bond or a double bond.

As used herein, the term "alkyl" refers to monovalent saturated aliphatic hydrocarbyl groups having from 1 to 12 carbon atoms, 1 to 10 carbon atoms, preferably 1 to 6 carbon atoms, and more preferably 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). The term "$C_x$ alkyl" refers to an alkyl group having x carbon atoms, wherein x is an integer, for example, $C_3$ refers to an alkyl group having 3 carbon atoms.

"Substituted alkyl" refers to an alkyl group having from 1 to 5, preferably 1 to 3, or more preferably 1 to 2 substituents selected from the group consisting of alkoxy, $R^{20}$—C(O)—, —NR$^{20}$C(O)R$^{20}$, $R^{20}$—C(O)O—, —NR$^{20}$R$^{20}$, —C(O)NR$^{20}$R$^{20}$, —C(S)NR$^{20}$R$^{20}$, —NR$^{20}$C(O)NR$^{20}$R$^{20}$, —NR$^{20}$C(S)NR$^{20}$R$^{20}$, —O—C(O)NR$^{20}$R$^{20}$, —S(O)$_2$NR$^{20}$R$^{20}$, —O—S(O)$_2$NR$^{20}$R$^{20}$, —NR$^{20}$—S(O)$_2$NR$^{20}$R$^{20}$, —C(=NR$^{20}$)NR$^{20}$R$^{20}$, aryl, aryloxy, arylthio, azido, carboxyl, —C(O)O—R$^{21}$, —NR$^{20}$—C(O)O—R$^{21}$, —O—C(O)O—R$^{21}$, cyano, cycloalkyl, cycloalkyloxy, cycloalkylthio, —NR$^{20}$C(=NR$^{20}$)N(R$^{20}$)$_2$, halo, hydroxy, hydroxyamino, alkoxyamino, —NR$^{20}$NR$^{20}$R$^{20}$, heteroaryl, heteroaryloxy, heteroarylthio, heterocyclic, heterocyclyloxy, heterocyclylthio, nitro, spirocycloalkyl,
$SO_3H$, —OS(O)$_2$—R$^{21}$, —S(O)$_2$—R$^{21}$, —C(S)—R$^{21}$, thiocyanate, thiol, and alkylthio; each R$^{20}$ is independently selected from the group consisting of hydrogen, alkyl, cycloalkyl, aryl, heteroaryl, and heterocycle, or two R$^{20}$ groups attached to a common atom are optionally joined together with the atom bound thereto to form a heterocycle; and each R$^{21}$ is independently selected from the group consisting of alkyl, cycloalkyl, aryl, heteroaryl, and heterocycle.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkoxy, —C(O)—R$^{20}$, —NR$^{20}$C(O)R$^{20}$, R$^{20}$—C(O)O—, —NR$^{20}$R$^{20}$, —C(O)NR$^{20}$R$^{20}$, —C(S)NR$^{20}$R$^{20}$, —NR$^{20}$C(O)NR$^{20}$R$^{20}$, —NR$^{20}$C(S)NR$^{20}$R$^{20}$, —O—C(O)NR$^{20}$R$^{20}$, —S(O)$_2$NR$^{20}$R$^{20}$, —O—S(O)$_2$NR$^{20}$R$^{20}$, —NR$^{20}$—S(O)$_2$NR$^{20}$R$^{20}$, —C(=NR$^{20}$)NR$^{20}$R$^{20}$, aryl, aryloxy, arylthio, azido, carboxyl, —C(O)O—R$^{21}$, —NR$^{20}$—C(O)O—R$^{21}$, —O—C(O)O—R$^{21}$, cyano, cycloalkyl, cycloalkyloxy, cycloalkylthio), —NR$^{20}$C(=NR$^{20}$)N(R$^{20}$)$_2$, halo, hydroxy, hydroxyamino, alkoxyamino, —NR$^{20}$NR$^{20}$R$^{20}$, heteroaryl, heteroaryloxy, heteroarylthio, heterocyclic, heterocyclyloxy, heterocyclylthio, nitro, spirocycloalkyl,
$SO_3H$, —OS(O)$_2$—R$^{21}$, —S(O)$_2$—R$^{21}$, —C(S)—R$^{21}$, thiocyanate, thiol, and alkylthio; each R$^{20}$ is independently selected from the group consisting of hydrogen, alkyl, cycloalkyl, aryl, heteroaryl, and heterocycle, or two R$^{20}$ groups attached to a common atom are optionally joined together with the atom bound thereto to form a heterocycle; and each R$^{21}$ is independently selected from the group consisting of alkyl, cycloalkyl, aryl, heteroaryl, and heterocycle.

"Cyano" refers to the group —CN.

"Cycloalkyl" refers to cyclic alkyl groups of from 3 to 10 or 3 to 8 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl.

"Substituted cycloalkyl" refers to a cycloalkyl group having from 1 to 5 or preferably 1 to 3 substituents selected from the group consisting of oxo, thione, alkyl, substituted alkyl, alkoxy, —C(O)—R$^{20}$, —NR$^{20}$C(O)R$^{20}$, R$^{20}$—C(O)O—, —NR$^{20}$R$^{20}$, —C(O)NR$^{20}$R$^{20}$, —C(S)NR$^{20}$R$^{20}$, —NR$^{20}$C(O)NR$^{20}$R$^{20}$, —NR$^{20}$C(S)NR$^{20}$R$^{20}$, —O—C(O)NR$^{20}$R$^{20}$, —S(O)$_2$NR$^{20}$R$^{20}$, —O—S(O)$_2$NR$^{20}$R$^{20}$, —NR$^{20}$—S(O)$_2$NR$^{20}$R$^{20}$, —C(=NR$^{20}$)NR$^{20}$R$^{20}$, aryl, aryloxy, arylthio, azido, carboxyl, —C(O)O—R$^{21}$, —NR$^{20}$—C(O)O—R$^{21}$, —O—C(O)O—R$^{21}$, cyano, cycloalkyl, cycloalkyloxy, cycloalkylthio, —NR$^{20}$C(=NR$^{20}$)N(R$^{20}$)$_2$, halo, hydroxy, hydroxyamino, alkoxyamino, —NR$^{20}$NR$^{20}$R$^{20}$, heteroaryl, heteroaryloxy, heteroarylthio, heterocyclic, heterocyclyloxy, heterocyclylthio, nitro, spirocycloalkyl,
$SO_3H$, —OS(O)$_2$—R$^{21}$, —S(O)$_2$—R$^{21}$, —C(S)—R$^{21}$, thiocyanate, thiol, and alkylthio; each R$^{20}$ is independently selected from the group consisting of hydrogen, alkyl, cycloalkyl, aryl, heteroaryl, and heterocycle, or two R$^{20}$ groups attached to a common atom are optionally joined together with the atom bound thereto to form a heterocycle; and each R$^{21}$ is independently selected from the group consisting of alkyl, cycloalkyl, aryl, heteroaryl, and heterocycle.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Heteroaryl" refers to an aromatic group of from 5 to 14 ring atoms, including from 1 to 10 carbon atoms and 1 to 4 heteroatoms selected from the group consisting of oxygen, nitrogen and sulfur. In some embodiments, heteroaryl comprises 5, 6, or 7 ring atoms, including 1 to 4 heteroatoms. Such heteroaryl groups can have a single ring (e.g., pyridyl, pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, and/or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heterocycle" or "heterocyclic" or "heterocycloalkyl" or "heterocyclyl" refers to a saturated or partially saturated, but not aromatic, group having from 3 to 14 ring atoms, including from 1 to 10 ring carbon atoms and from 1 to 4 ring heteroatoms selected from the group consisting of nitrogen, sulfur, or oxygen. In some embodiments, heteroaryl comprises 3, 4, 5, 6 or 7 ring atoms, including 1 to 4 heteroatoms. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

Substituted groups of this invention, as set forth above, do not include polymers obtained by an infinite chain of substituted groups. At most, any substituted group can be substituted up to five times.

"Ibogaine" refers to the compound:

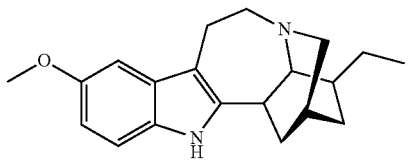

It should be understood that where "ibogaine" is mentioned herein, one more polymorphs of ibogaine can be utilized and are contemplated. Ibogaine is isolated from *Tabernanth iboga*, a shrub of West Africa. Ibogaine can also be synthesized using known methods. See, e.g., Büchi, et al. (1966), J. Am. Chem Society, 88(13), 3099-3109.

"Pharmaceutically acceptable composition" refers to a composition that is suitable for administration to a mammal, particularly, a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

"Therapeutically effective amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating anxiety disorders, impulse control disorder, and/or anger/violence-related disorders, refers to an amount of the agent that attenuates the anxiety disorder, impulse control disorder, or anger/violence-related disorders, and/or symptoms thereof, in the patient. A therapeutically effective amount of an agent, in the context of regulating food intake and/or controlling food cravings, refers to an amount of the agent that reduces the patient's food intake and/or reduces food cravings in the patient.

The therapeutically effective amount of the compound may be higher or lower, depending on the route of administration used. For example, when direct blood administration (e.g., sublingual, pulmonary, buccal, or intranasal delivery) is used, a lower dose of the compound is administered. In one aspect, a therapeutically effective amount of ibogaine or derivative is from about 50 ng to less than about 100 µg per kg of body weight. Where other routes of administration are used, a higher dose of the compound is administered. In one embodiment, the therapeutically effective amount of the compound is from about 1 mg to about 4 mg per kg of body weight per day.

A "therapeutic level" of a drug is an amount of ibogaine or an ibogaine derivative that is sufficient to treat the anxiety disorder, impulse control disorder, anger/violence-related disorders, or to regulate food intake, but not high enough to pose any significant risk to the patient. Therapeutic levels of drugs can be determined by tests that measure the actual concentration of the compound in the blood of the patient. This concentration is referred to as the "serum concentration." Where the serum concentration of ibogaine is mentioned, it is to be understood that the term "ibogaine" encompasses any form of ibogaine, including derivatives thereof.

The term "dose" refers to a range of ibogaine, ibogaine derivative, or pharmaceutical salt or solvate thereof that provides a therapeutic serum level of ibogaine when given to a patient in need thereof. The dose is recited in a range, for example from about 20 mg to about 120 mg, and can be expressed either as milligrams or as mg/kg body weight. The attending clinician will select an appropriate dose from the range based on the patient's weight, age, degree of addiction, health, and other relevant factors, all of which are well within the skill of the art.

The term "unit dose" refers to a dose of drug that is given to the patient to provide therapeutic results, independent of the weight of the patient. In such an instance, the unit dose is sold in a standard form (e.g., 20 mg tablet). The unit dose may be administered as a single dose or a series of subdoses. In some embodiments, the unit dose provides a standardized level of drug to the patient, independent of weight of patient. Many medications are sold based on a dose that is therapeutic to all patients based on a therapeutic window. In such cases, it is not necessary to titrate the dosage amount based on the weight of the patient.

"Treatment", "treating", and "treat" are defined as acting upon a disease, disorder, or condition with an agent to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to, treating an anxiety disorder, impulse control disorder, anger/violence-related disorders, or regulating food intake. Anxiety disorders or impulse control disorders occurring as a result of withdraw and/or use of an opiate or other illicit drug or substance is not within the scope of this invention.

As used herein, the term "QT interval" refers to the measure of the time between the start of the Q wave and the end of the T wave in the electrical cycle of the heart. Prolongation of the QT interval refers to an increase in the QT interval. Measurement of the QT interval, and determination of the interval, can be performed by any method.

As used herein, the term "patient" refers to mammals and includes humans and non-human mammals.

A "pharmaceutically acceptable solvate" or "hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

Herein the term solvate is taken to mean that a solid-form of a compound that crystallizes with one or more molecules of solvent trapped inside. A few examples of solvents that can be used to create solvates, such as pharmaceutically acceptable solvates, include, but are certainly not limited to, water, methanol, ethanol, isopropanol, butanol, C1-C6 alcohols in general (and optionally substituted), tetrahydrofuran, acetone, ethylene glycol, propylene glycol, acetic acid, formic acid, water, and solvent mixtures thereof. Other such biocompatible solvents which may aid in making a pharmaceutically acceptable solvate are well known in the art and applicable to the present invention. Additionally, various organic and inorganic acids and bases can be added or even used alone as the solvent to create a desired solvate. Such acids and bases are known in the art. When the solvent is water, the solvate can be referred to as a hydrate. Further, by being left in the atmosphere or recrystallized, the compounds of the present invention may absorb moisture, may include one or more molecules of water in the formed crystal, and thus become a hydrate. Even when such hydrates are formed, they are included in the term "solvate". Solvate also is meant to include such compositions where another compound or complex co-crystallizes with the compound of interest.

Compositions of the Invention

As will be apparent to the skilled artisan upon reading this disclosure, this invention provides compositions for treating an anxiety disorder, impulse control disorder, anger/violence-related disorders, or regulating food intake, in a subject, comprising ibogaine, ibogaine derivatives, prodrugs of ibogaine, pharmaceutically acceptable salts and/or solvates of each thereof. This invention further provides compositions for treating, attenuating, or preventing anxiety disorder, impulse control disorder, anger/violence-related disorders, symptoms thereof, or food cravings in a subject, comprising ibogaine, ibogaine derivatives, prodrugs of ibogaine, pharmaceutically acceptable salts and/or solvates of each thereof.

In some embodiments, the composition is formulated for sublingual, intranasal, or intrapulmonary delivery. In one aspect, the invention provides a pharmaceutical composition comprising a pharmaceutically effective amount of ibogaine and a pharmaceutically acceptable excipient, wherein the therapeutically effective amount of ibogaine is an amount that delivers an aggregate amount of ibogaine of about 50 ng to less than about 100 μg per kg body weight per day. In some aspects, the therapeutically effective amount of ibogaine is an amount that delivers an aggregate amount of ibogaine of about 50 ng to about 50 μg per kg body weight per day. In some aspects, the therapeutically effective amount of ibogaine is an amount that delivers an aggregate amount of ibogaine of about 50 ng to about 10 μg per kg body weight per day. In some aspects, the therapeutically effective amount of ibogaine is an amount that delivers an aggregate amount of ibogaine of about 50 ng to about 1 μg per kg body weight per day. In some aspects, the composition is formulated for administration once per day. In some aspects, the composition is formulated for administration two or more times per day. The ranges include both extremes as well as any subranges there between.

In some embodiments, the composition is formulated for oral, buccal, transdermal, internal, pulmonary, rectal, nasal, vaginal, lingual, intravenous, intraarterial, intramuscular, intraperitoneal, intracutaneous or subcutaneous delivery.

In one embodiment, the therapeutically effective amount of the compound is from about 1 mg to about 4 mg per kg body weight per day. In another embodiment, the therapeutically effective amount of the compound is from about 1 mg to about 3 mg per kg body weight per day. In another embodiment, the therapeutically effective amount of the compound is from about 1 mg to about 2 mg per kg body weight per day. In another embodiment, the therapeutically effective amount of the compound is from about 1.3 mg to about 3 mg per kg body weight per day. In another embodiment, the therapeutically effective amount of the compound is from about 1.5 mg to about 3 mg per kg body weight per day. In another embodiment, the therapeutically effective amount of the compound is from about 1.7 mg to about 3 mg per kg body weight per day. In another embodiment, the therapeutically effective amount of the compound is from about 1.3 mg to about 4 mg per kg body weight per day. In another embodiment, the therapeutically effective amount of the compound is from about 1.5 mg to about 4 mg per kg body weight per day. In another embodiment, the therapeutically effective amount of the compound is about about 2 mg per kg body weight per day. The ranges include both extremes as well as any subrange or subvalue there between.

In one embodiment, the therapeutically effective amount of the compound is about 4 mg/kg body weight per day. In one embodiment, the therapeutically effective amount of the compound is about 3 mg/kg body weight per day. In another embodiment, the therapeutically effective amount of the compound is about 2 mg per kg body weight per day. In another embodiment, the therapeutically effective amount of the compound is about 1.7 mg per kg body weight per day. In another embodiment, the therapeutically effective amount of the compound is about 1.5 mg per kg body weight per day. In another embodiment, the therapeutically effective amount of the compound is about 1.2 mg per kg body weight per day. In another embodiment, the therapeutically effective amount of the compound is about 1 mg per kg body weight per day.

In some embodiments, the ibogaine or ibogaine derivative is represented by Formula I:

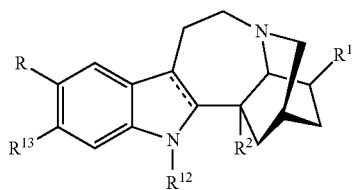

I or a pharmaceutically acceptable salt and/or solvate thereof, wherein

R is H, halo, $C_1$-$C_3$ alkyl, substituted $C_1$-$C_3$ alkyl, $OR^{10}$, $NH_2$, $NHR^{10}$, $NR^{10}R^{11}$, $NHC(O)R^{10}$, or $NR^{10}C(O)R^{11}$;

$R^1$ is H, $C_1$-$C_3$ alkyl, substituted $C_1$-$C_3$ alkyl, $C_1$-$C_3$ alkoxy, $CH_2$—X—$CH_3$, or $(CH_2)_m R^3$;

$R^2$ is H, COOH, $COOR^4$, $(CH_2)_n OH$, $CH(OH)R^5$, $CH_2 OR^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;

$R^3$ is $C_1$-$C_3$ alkyl, benzyl, substituted $C_1$-$C_3$ alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, $O(CH_2)_p O(CH_2)_q O(CH_2)_r CH_3$ or $NR^8 C(O)R^9$;

$R^4$ is $C_1$-$C_6$ alkyl or $(CH_2CH_2O)_n CH_3$;

$R^5$, $R^6$, $R^7$, $R^8$, $R^9$, $R^{10}$, and $R^{11}$ are independently alkyl or substituted alkyl;

$R^{12}$ is H, alkyl, or substituted alkyl;

$R^{13}$ is H, $OR^{10}$, alkyl, or substituted alkyl;

X is O or NH;

Y is O or S;

m is an integer selected from 0-8;

each of n, p and q is 1, 2 or 3; and r is 0, 1 or 2.

In some embodiments, the ibogaine or ibogaine derivative is represented by Formula II:

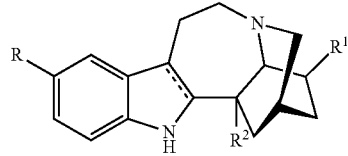

II or a pharmaceutically acceptable salt and/or solvate thereof, wherein

R is hydrogen or $C_1$-$C_3$ alkoxy, $R^1$ is hydrogen, $C_1$-$C_3$ alkyl, $C_1$-$C_3$ alkoxy, $(CH_2)_m OC(O)$ alkyl, $(CH_2)_m OH$, $(CH_2)_m Oalkyl$, $(CH_2)_m O(CH_2)_p O (CH_2)_q O(CH_2)_r CH_3$ or $CH_2$—Y—$CH_3$ where each of m, p and q is 1, 2 or 3; and r is 0, 1 or 2, Y is O or NH, and $R^2$ is H, $(CH_2)_n OH$, COOH, or $COOR^4$, where $R^4$ is $C_1$-$C_6$ alkyl or $(CH_2CH_2O)_n CH_3$, where n is 1, 2, or 3.

In one embodiment, R is methoxy. In one embodiment, $R^1$ is ethyl. In one embodiment, $R^1$ is methoxy. In one embodiment, $R^1$ is $CH_2$—Y—$CH_3$ where Y is O. In one embodiment, $R^1$ is $CH_2$—Y—$CH_3$ where Y is NH. In one embodiment, $R^2$ is hydrogen. In one embodiment, In one embodiment, $R^2$ is $COOR^4$ and $R^4$ is methyl. In one embodiment, n=1. In a preferred embodiment, R, $R^1$ and $R^2$ are all not hydrogen. In one embodiment, when R is methoxy and $R^1$ is hydrogen, then $R^2$ is COOH or $COOR^4$. In another embodiment, when R is methoxy and $R^1$ is hydrogen, then X is $COOR^4$ where $R^4$ is $(CH_2CH_2O)CH_3$.

In one embodiment, $R^{12}$ is hydrogen.

In one embodiment, $R^1$ is H. In one embodiment, $R^1$ is $C_1$-$C_3$ alkyl, such as ethyl. In one embodiment, $R^1$ is $CH_2CH_2OH$. In one embodiment, $R^1$ is $CH_2CH_2OCH_3$. In one embodiment, $R^1$ is $CH_2CH_2OCH_2Ph$. In one embodiment, le is $CH_2CH_2OC(O)$alkyl. In one embodiment, $R^1$ is $CH_2CH_2O(CH_2)_p O(CH_2)_q O(CH_2)_r CH_3$.

In one embodiment, $R^2$ is $CH_2OH$ and $CH(OH)R^5$. In one embodiment, $R^2$ is $CH_2OR^5$. In one embodiment, $R^2$ is $CO_2R^5$. In one embodiment, $R^2$ is $C(O)NH_2$, $C(O)NHR^5$, or $C(O)NR^5R^6$. In one embodiment, $R^2$ is $C(O)NHNH_2$, $C(O)NHNHR^5$, $C(O)NR^5NH_2$, $C(O)NHNR^5R^6$, $C(O)NH^5NHR^6$, or $C(O)NR^5NR^6R^7$. In one embodiment, $R^2$ is $C(O)NHNH(C(O)R^5)$, $C(O)NHNR^5(C(O)R^6)$, $C(O)NR^5NH(C(O)R^6)$, or $C(O)NR^5NR^6(C(O)R^7)$. In one embodiment, $R^2$ is $C(O)R^5$.

In the various method, formulation and kit aspects and embodiments, in one embodiment a compound utilized herein is represented by, or ibogaine as used herein is replaced by, a compound Formula I:

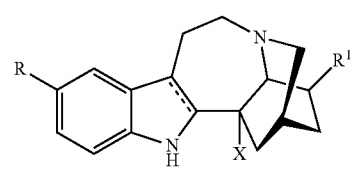

I wherein

R is hydrogen or $C_1$-$C_3$-alkoxy, $R^1$ is hydrogen, $C_1$-$C_3$-alkyl, $C_1$-$C_3$ alkoxy, or $CH_2$—Y— $CH_3$ where Y is O or NH, and X is H, COOH, or $COOR^2$, where $R^2$ is $C_1$-$C_6$ alkyl or $(CH_2CH_2O)_n CH_3$, where n=1 to 3.

In another embodiment, ibogaine or a pharmaceutically acceptable salt and/or solvate thereof is utilized. In another embodiment, ibogaine or a pharmaceutically acceptable salt and/or solvate thereof is utilized. In another embodiment, the ibogaine, ibogaine derivative, is chosen from the group consisting of ibogaine, coronaridine, ibogamine, voacangine, 18-methoxycoronaridine, 2-methoxyethyl-18-methoxycoronaridinate, 18-methylaminocoronaridine or a pharmaceutically acceptable salt and/or solvate thereof.

In another embodiment, the compound utilized herein is chosen from the group consisting of ibogaine, coronaridine, ibogamine, voacangine, 18-methoxycoronaridine, 2-methoxyethyl-18-methoxycoronaridinate, 18-methylaminocoronaridine and a pharmaceutically acceptable salt and/or solvate.

In another embodiment, the compound utilized herein is selected from the group consisting of 16-hydroxymethyl-18-hydroxyibogaline, 16-hydroxymethyl-18-methoxyibogaline, 16-ethoxycarbonyl-18-hydroxyibogaline laurate, and 16-ethoxycarbonyl-18-hydroxyibogaline methoxyethoxymethyl ether and a pharmaceutically acceptable salt and/or solvate thereof.

In one embodiment, the ibogaine derivative is represented by Formula II:

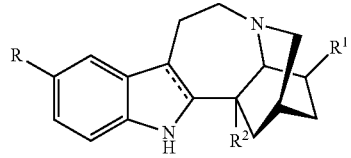

II or a pharmaceutically acceptable salt and/or solvate thereof, wherein
R is hydrogen or $C_1$-$C_3$ alkoxy;
$R^1$ is hydrogen, $C_1$-$C_3$ alkyl, $C_1$-$C_3$ alkoxy, $(CH_2)_mOC(O)$alkyl, $(CH_2)_mOH$, $(CH_2)_mOalkyl$, $(CH_2)_mO(CH_2)_pO(CH_2)_qO(CH_2)_rCH_3$ or $CH_2$—Y—$CH_3$ where each of m, p and q is 1, 2 or 3; and r is 0, 1 or 2, Y is O or NH; and $R^2$ is H, $(CH_2)_nOH$, COOH, or $COOR^4$, where $R^4$ is $C_1$-$C_6$ alkyl or $(CH_2CH_2O)_nCH_3$, where n is 1, 2, or 3.

In one embodiment, the ibogaine derivative is selected from the group consisting of coronaridine, ibogamine, voacangine, 18-methoxycoronaridine, 2-Methoxyethyl-18-methoxycoronaridinate, and 18-Methylaminocoronaridine.

In one embodiment, the ibogaine derivative is selected from the group consisting of 16-hydroxymethyl-18-hydroxyibogaline, 16-hydroxymethyl-18-methoxyibogaline, 16-ethoxycarbonyl-18-hydroxyibogalinelaurate, and 16-ethoxycarbonyl-18-hydroxyibogaline methoxyethoxymethyl ether.

In one embodiment, the compound is of Formula IA:

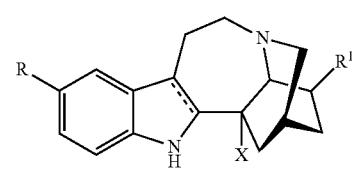

IA wherein
R is hydrogen or $C_1$-$C_3$-alkoxy,
$R^1$ is hydrogen, $C_1$-$C_3$-alkyl, $C_1$-$C_3$ alkoxy, or $CH_2$—Y—$CH_3$ where Y is O or NH, and
X is H, COOH, or $COOR^2$, where $R^2$ is $C_1$-$C_6$ alkyl or $(CH_2CH_2O)_nCH_3$, where n=1 to 3.

In another embodiment, the ibogaine derivative is represented by Formula II:

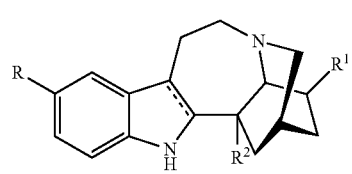

II or a pharmaceutically acceptable salt and/or solvate thereof, wherein
R is $OCH_3$;
$R^1$ is $CH_2CH_3$; and
$R^2$ is $COOR^4$, where $R^4$ is $(CH_2CH_2O)_nCH_3$, where n is 1.

When replacing ibogaine, the compounds of formula I, II, and subformulas thereof as utilized herein exclude ibogaine.

In a preferred embodiment, the compound utilized herein is:

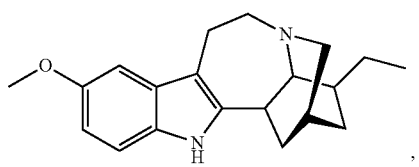

, a pharmaceutically acceptable salt thereof, or a solvate of each thereof.

In some embodiments, the ibogaine or ibogaine derivative is selected from:

| Name | Structure |
| --- | --- |
| coronaridine | ![structure with CO₂CH₃] |

-continued

| Name | Structure |
|---|---|
| 18-hydroxycoronaridine | *(structure)* |
| 18-methoxycoronaridine | *(structure)* |
| 18-benzyloxycoronaridine | *(structure)* |
| 18-hydroxycoronaridine laurate | *(structure)* |
| 18-hydroxycoronaridine methoxyethoxymethyl ether | *(structure)* |
| 18-hydroxycoronaridine acetate | *(structure)* |
| voacangine | *(structure)* |
| 18-hydroxyvoacangine | *(structure)* |

| Name | Structure |
|---|---|
| 18-methoxyvoacangine | 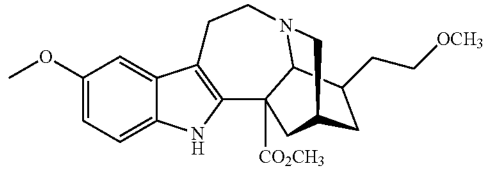 |
| 18-benzyloxyvoacangine | 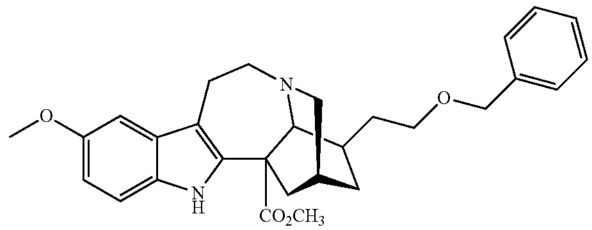 |
| 18-hydroxyvoacangine laurate | 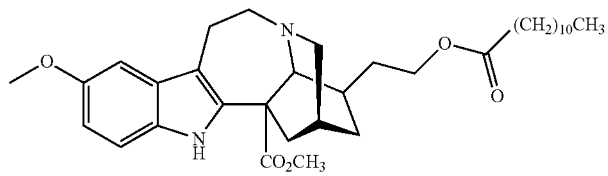 |
| 18-hydroxyvoacangine acetate | 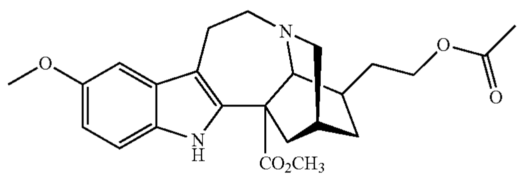 |
| 18-hydroxyvoacangine methoxyethoxymethyl ether | 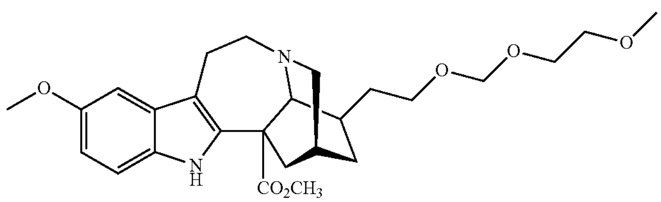 |
| conopharyngine | 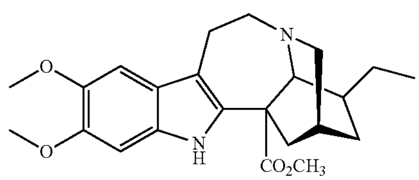 |
| 18-hydroxyconopharyngine | 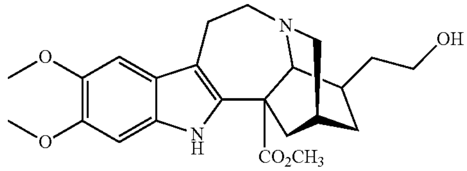 |
| 18-methoxyconopharyngine | 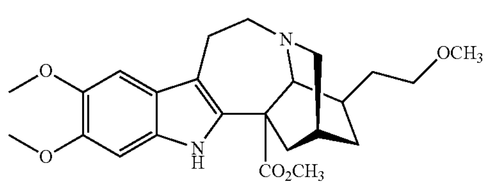 |

| Name | Structure |
|---|---|
| 18-benzyloxyconopharyngine | 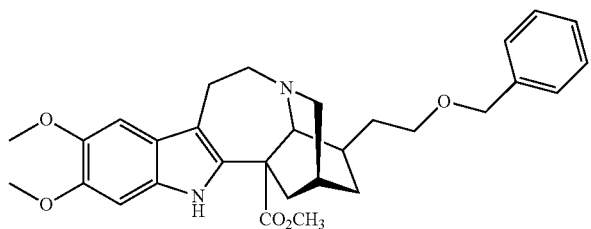 |
| 18-hydroxyconopharyngine laurate | 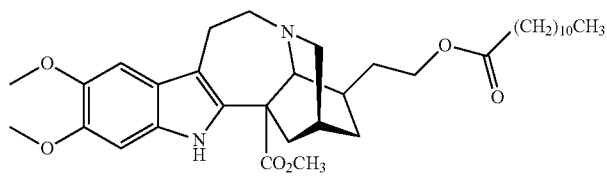 |
| 18-hydroxyconopharyngine acetate | 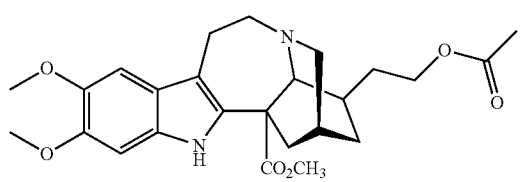 |
| 18-hydroxyconopharyngine methoxyethoxymethyl ether | 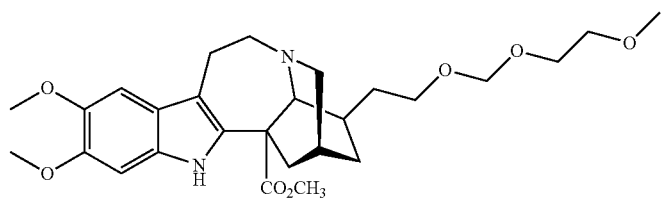 |
| ibogamine | 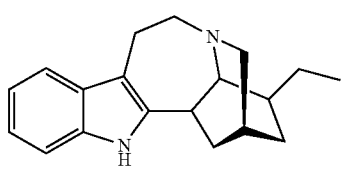 |
| 16-ethoxycarbonyl-18-hydroxyibogamine | 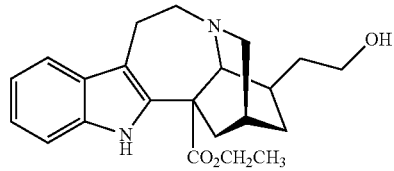 |
| 16-hydroxymethyl-18-hydroxyibogamine | 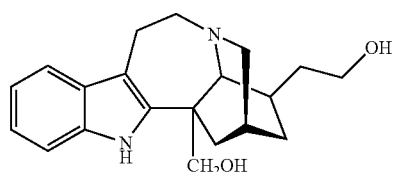 |
| 16-ethoxycarbonyl-18-methoxyibogamine | 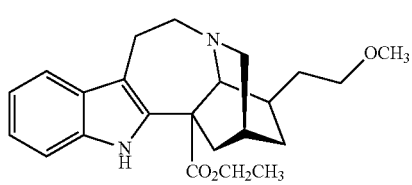 |

| Name | Structure |
|---|---|
| 16-hydroxymethyl-18-methoxyibogamine | 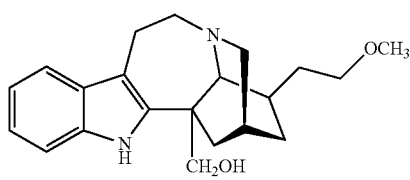 |
| 16-ethoxycarbonyl-18-benzyloxyibogamine | 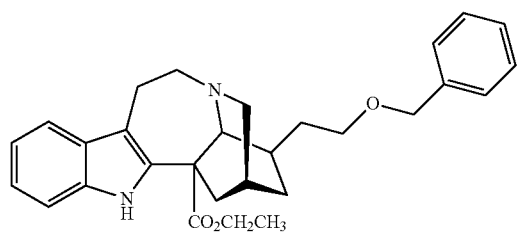 |
| 16-ethoxycarbonyl-18-hydroxyibogamine laurate | 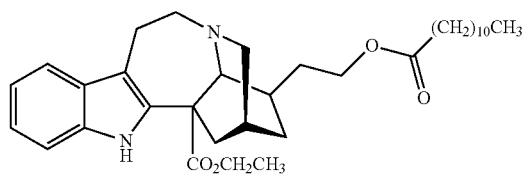 |
| 16-ethoxycarbonyl-18-hydroxyibogamine acetate | 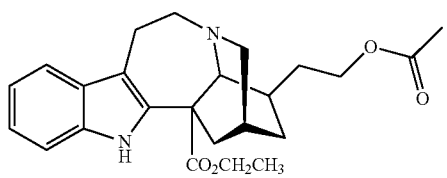 |
| 16-ethoxycarbonyl-18-hydroxyibogamine methoxyethoxymethyl ether | 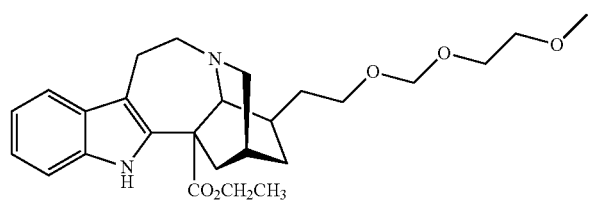 |
| ibogaine | 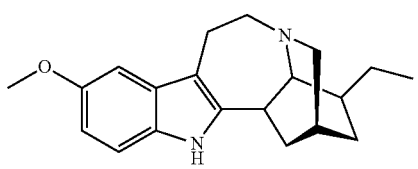 |
| 16-ethoxycarbonyl-18-hydroxyibogaine | 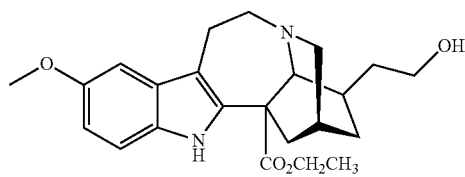 |
| 16-hydroxymethyl-18-hydroxyibogaine | 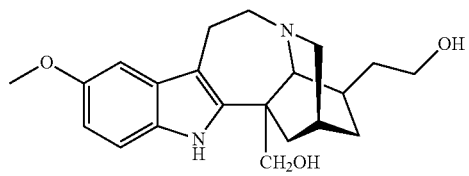 |

-continued
| Name | Structure |
|---|---|
| 16-ethoxycarbonyl-18-methoxyibogaine | 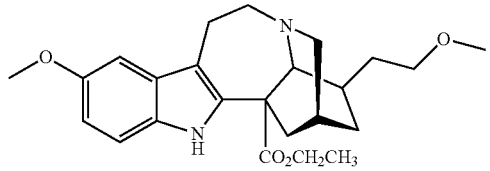 |
| 16-hydroxymethyl-18-methoxyibogaine | 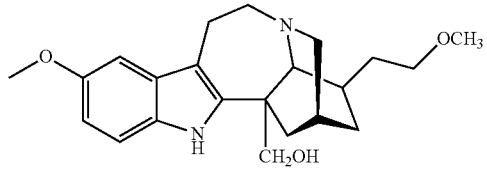 |
| 16-ethoxycarbonyl-18-benzyloxyibogaine | 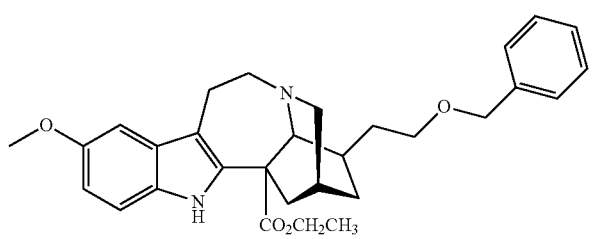 |
| 16-ethoxycarbonyl-18-hydroxyibogaine laurate | 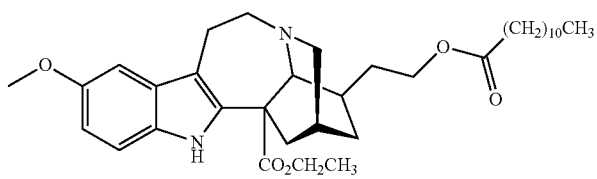 |
| 16-ethoxycarbonyl-18-hydroxyibogaine acetate | 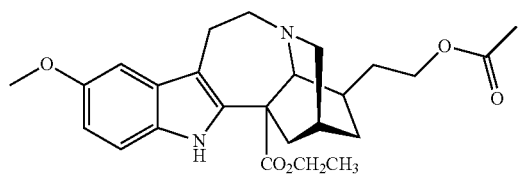 |
| 16-ethoxycarbonyl-18-hydroxyibogaine methoxyethoxymethyl ether | 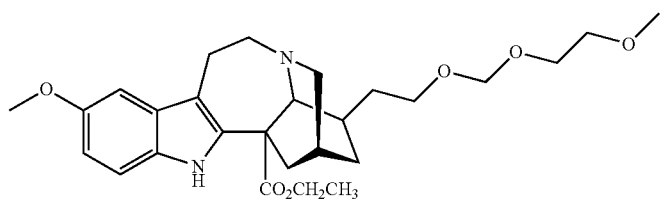 |
| ibogaline | 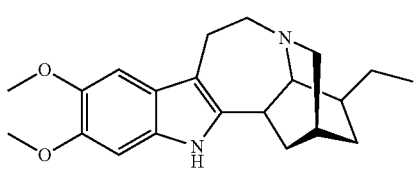 |
| 16-ethoxycarbonyl-18-hydroxyibogaline | 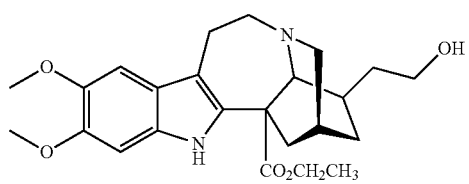 |

| Name | Structure |
|---|---|
| 16-hydroxymethyl-18-hydroxyibogaline | *(structure)* |
| 16-ethoxycarbonyl-18-methoxyibogaline | *(structure)* |
| 16-hydroxymethyl-18-methoxyibogaline | *(structure)* |
| 16-ethoxycarbonyl-18-benzyloxyibogaline | *(structure)* |
| 16-ethoxycarbonyl-18-hydroxyibogaline laurate | *(structure)* |
| 16-ethoxycarbonyl-18-hydroxyibogaline acetate | *(structure)* |
| 16-ethoxycarbonyl-18-hydroxyibogaline methoxyethoxymethyl ether | *(structure)* | and pharmaceutically acceptable salts and/or solvates thereof.

This invention is not limited to any particular chemical form of the compounds, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

In one embodiment, the ibogaine derivative is:

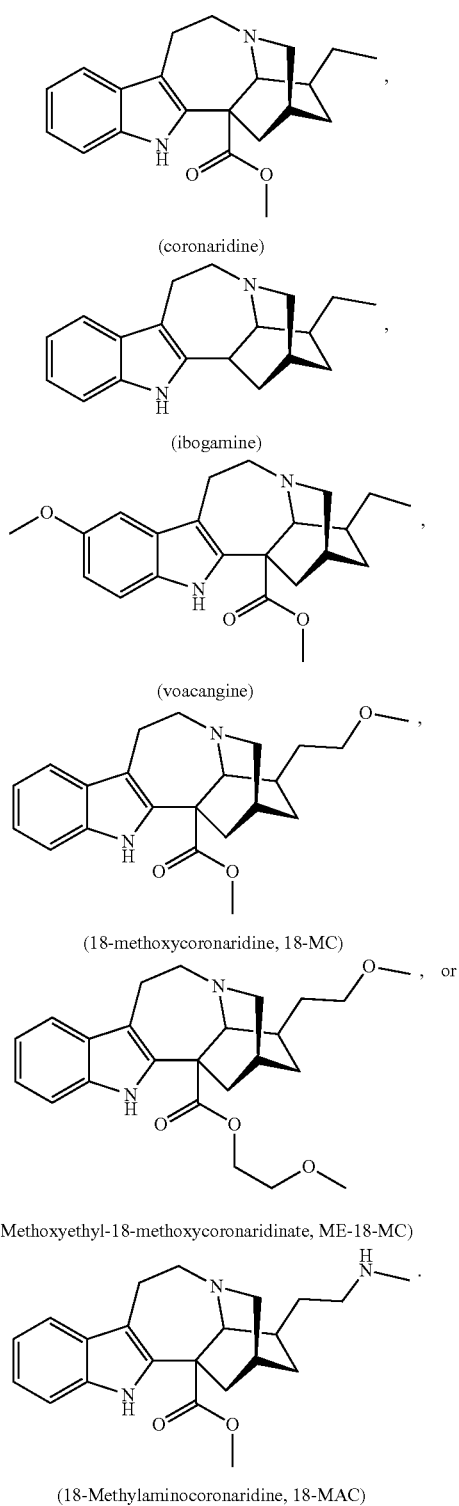

(coronaridine)

(ibogamine)

(voacangine)

(18-methoxycoronaridine, 18-MC)

(2-Methoxyethyl-18-methoxycoronaridinate, ME-18-MC)

(18-Methylaminocoronaridine, 18-MAC)

Methods of the Invention

As will be apparent to the skilled artisan upon reading this disclosure, this invention provides a method for treating anxiety disorder, impulse control disorder, anger/violence-related disorders, or regulating food intake in a patient in need thereof, comprising administering to the patient a therapeutically effective amount of ibogaine, an ibogaine derivative, or a pharmaceutically acceptable salt and/or solvate thereof. In a preferred embodiment, the patient is not addicted to cocaine or an opiate. Ibogaine derivatives include, but are not limited to, the compounds described in the "Compositions of the Invention" section above.

The following description of anxiety disorders and impulse control disorders is provided for the purpose of facilitating an understanding of the utility of the compounds and compositions of this invention. Disorders associated with violence and/or anger are included in these descriptions. The definitions of anxiety disorders and impulse control disorders given below are those listed in American Psychiatric Association, 2013, American Psychiatric Association, 1994a, or American Psychiatric Association, 1987. Additional information regarding these disorders can be found in these references, as well as other references cited below, all of which are hereby incorporated herein by reference.

Anxiety disorders include panic disorder, agoraphobia with or without history of panic disorder, specific phobia, social phobia, obsessive-compulsive disorder, post-traumatic stress disorder, acute stress disorder and generalized anxiety disorder. It is contemplated that the compounds of this invention will be effective in treating these disorders in patients who have been diagnosed as having such disorders.

This invention provides for a method of treating a patient suffering from anxiety which comprises administering to the patient an amount of any of the compounds described herein effective to treat the subject's anxiety.

It is contemplated that the compounds described herein will be effective in treating obsessions and compulsions in patients who have been diagnosed as having obsessive compulsive disorder based upon administration of appropriate tests, which may include, but are not limited to any of the following: Yale Brown Obsessive Compulsive Scale (YBOCS) (for adults), National Institute of Mental Health Global OCD Scale (NIMH GOCS), CGI-Severity of Illness scale. It is further contemplated that the compounds described herein will be effective in inducing improvements in certain of the factors measured in these tests, such as a reduction of several points in the YBOCS total score. It is also contemplated that the compounds described herein will be effective in preventing relapse of obsessive compulsive disorder and/or symptoms thereof.

This invention provides a method of treating obsessions and/or compulsions in a patient with obsessive compulsive disorder, which comprises administering to the patient a therapeutically effective amount of any of the compounds utilized herein effective to treat the subject's obsessions and/or compulsions.

It is contemplated that the compounds described herein will be effective in treating panic disorder in patients who have been diagnosed with panic disorder on the basis of frequency of occurrence of panic attacks, or by means of the CGI-Severity of Illness scale. It is further contemplated that the compounds described herein will be effective in inducing improvements in certain of the factors measured in these evaluations, such as a reduction in frequency or elimination of panic attacks, an improvement in the CGI-Severity of Illness scale or a CGI-Global Improvement score of 1 (very much improved), 2 (much improved) or 3 (minimally improved). It is also contemplated that the compounds described herein will be effective in preventing relapse of panic disorder.

This invention provides a method of treating panic disorder, with or without agoraphobia, in a subject, which comprises administering to the patient a therapeutically effective amount of any of the compounds utilized herein to treat the subject's panic disorder.

It is contemplated that the compounds described herein can be effective in treating social anxiety disorder in patients who have been diagnosed as having social anxiety disorder based upon the administration of any of the following tests: the Liebowitz Social Anxiety Scale (LSAS), the CGI-Severity of Illness scale, the Hamilton Rating Scale for Anxiety (HAM-A), the Hamilton Rating Scale for Depression (HAM-D), the axis V Social and Occupational Functioning Assessment Scale of DSM-IV, the axis II (ICD-10) World Health Organization Disability Assessment, Schedule 2 (DAS-2), the Sheehan Disability Scales, the Schneier Disability Profile, the World Health Organization Quality of Life-100 (WHOQOL-100), or other tests as described in Bobes, 1998, which is incorporated herein by reference. It is further contemplated that the compounds described herein will be effective in inducing improvements as measured by these tests, such as the a change from baseline in the Liebowitz Social Anxiety Scale (LSAS), or a CGI-Global Improvement score of 1 (very much improved), 2 (much improved) or 3 (minimally improved). It is also contemplated that the compounds described herein will be effective in preventing relapse of social anxiety disorder.

This invention provides a method of treating social anxiety disorder in a patient which comprises administering to the patient a therapeutically effective amount of any of the compounds utilized herein to treat the subject's social anxiety disorder.

It is contemplated that the compounds utilized herein can be effective in treating generalized anxiety disorder in patients who have been diagnosed as having this disorder based upon the diagnostic criteria described in DSM-IV or DSM-5. It is further contemplated that the compounds utilized herein will be effective in reducing symptoms of this disorder, such as the following: excessive worry and anxiety, difficulty controlling worry, restlessness or feeling keyed up or on edge, being easily fatigued, difficulty concentrating or mind going blank, irritability, muscle tension, or sleep disturbance. It is also contemplated that the compounds described herein will be effective in preventing relapse of general anxiety disorder.

The invention provides a method of treating generalized anxiety disorder in a subject, which comprises administering to the patient an amount of any of the compounds described herein effective to treat the subject's generalized anxiety disorder.

Impulse control disorders include pathological gambling (PG), kleptomania, trichotillomania (TTM), intermittent explosive disorder (IED), and pyromania. Impulse control disorders may also include pathological skin picking (PSP), compulsive sexual behavior (CSB), compulsive buying (CB), conduct disorder, antisocial personality disorder, oppositional defiant disorder, borderline personality disorder, attention deficit/hyperactivity disorder (ADHD, which includes attention deficit disorder, ADD), schizophrenia, mood disorders, paraphilia, and internet addiction. Symptoms of impulse control disorders include: repetitive participation in behavior despite adverse consequences, diminished control over the behavior, an urge/impulse to engage in the behavior, and feelings of pleasure while participating in the behavior.

It is contemplated that the compounds utilized herein can be effective in treating impulse control disorders in patients who have at least one impulse control disorder based upon the diagnostic criteria described in DSM-IV or DSM-5. It is further contemplated that the compounds utilized herein will be effective in reducing symptoms of this disorder, including impulsivity or lack of self-control. It is also contemplated that the compounds described herein will be effective in preventing relapse of the impulse control disorder.

It is contemplated that the compounds utilized herein can be effective in treating ADHD or ADD in patients who have the disorder, based upon the diagnostic criteria described in DSM-IV or DSM-5. It is further contemplated that the compounds utilized herein will be effective in reducing symptoms of this disorder, including impulsivity or lack of self-control. It is also contemplated that the compounds described herein will be effective in preventing relapse of ADD or ADHD.

It is contemplated that the compounds utilized herein can be effective in treating schizophrenia in patients who have the disorder, based upon the diagnostic criteria described in DSM-IV or DSM-5. Schizophrenia is characterized by delusions, hallucinations, disorganized speech and behavior, and other symptoms that cause social or occupational dysfunction. It is further contemplated that the compounds utilized herein will be effective in reducing symptoms of this disorder. It is also contemplated that the compounds described herein will be effective in preventing relapse of schizophrenia.

It is contemplated that the compounds described herein will be effective in treating non-suicidal self injury disorder in patients who have been diagnosed with this disorder based on the patient's exhibition of symptoms including deliberate tissue injury without suicidal intent (e.g., cutting, burning, self-poisoning, or self-mutilation). It is further contemplated that the compounds described herein will be effective in inducing improvements in certain of these factors, such as a reduction in frequency or elimination of self injury. It is also contemplated that the compounds described herein will be effective in preventing relapse of non-suicidal self injury disorder.

This invention provides a method of treating non-suicidal self injury disorder in a subject, which comprises administering to the patient a therapeutically effective amount of any of the compounds utilized herein to treat the subject's non-suicidal self injury disorder.

It is contemplated that the compounds described herein will be effective in treating Munchausen syndrome in patients who have been diagnosed with this disorder based on the patient's propensity for feigning disease, illness, or psychological trauma to draw attention, sympathy, or reassurance to themselves. Symptoms may include frequent hospitalizations, knowledge of several illnesses, frequent requests for medication (e.g., pain killers), willingness to undergo extensive surgery, few to no visitors during hospitalizations, and exaggerated or fabricated stories about multiple medical problems. It is further contemplated that the compounds described herein will be effective in inducing improvements in certain of these factors, such as a reduction in frequency or elimination of one or more symptoms. It is also contemplated that the compounds described herein will be effective in preventing relapse of Münchausen syndrome. Münchausen syndrome also includes Münchausen syndrome by proxy, in which a caregiver exaggerates, fabricates, or induces illness in someone in his/her care.

This invention provides a method of treating Münchausen syndrome in a subject, which comprises administering to the patient a therapeutically effective amount of any of the compounds utilized herein to treat the subject's Münchausen syndrome.

It is contemplated that the compounds described herein will be effective in treating disruptive mood dysregulation disorder in patients who have been diagnosed with this disorder on the basis of severe and recurrent temper outbursts, grossly out of proportion to the stimulus or situation, as well as a persistent irritable/angry mood most of the time. It is further contemplated that the compounds described herein will be effective in inducing improvements in certain of these factors, such as a reduction in frequency or elimination of temper outbursts and/or an improvement in mood. It is also contemplated that the compounds described herein will be effective in preventing relapse of disruptive mood dysregulation disorder disorder.

This invention provides a method of treating disruptive mood dysregulation disorder in a subject, which comprises administering to the patient a therapeutically effective amount of any of the compounds utilized herein to treat the subject's disruptive mood dysregulation disorder.

It is contemplated that the compounds utilized herein can be effective in reducing the frequency, intensity, and duration of anger and/or violence in individuals prone to one or both. Although anger and violence disorders other than those associated with other disorders (e.g., as described above) are not outlined in DSM IV or DSM 5, many health professionals recognize that such disorders are associated with significant dysfunction. Anger management training and other psychosocial treatments are often used in an effort to treat these individuals.

This invention provides a method of treating anger- and/or violence-related disorder in a subject, which comprises administering to the patient a therapeutically effective amount of any of the compounds utilized herein to treat the subject's anger- and/or violence-related disorder.

It is contemplated that the compounds utilized herein can be effective in regulating food intake and/or reducing food cravings in patients in need thereof. In some embodiments, the patient is overweight. In some embodiments, the patient is obese. In some embodiments, the patient exhibits comorbidities associated with overweight/obesity, for example coronary heart disease, high blood pressure, stroke, type 2 diabetes, abnormal levels of blood fats, metabolic syndrome, cancer, osteoarthritis, sleep apnea, reproductive issues, and/or gallstones.

This invention provides a method of regulating food intake and/or reducing food cravings in a subject, which comprises administering to the patient a therapeutically effective amount of any of the compounds utilized herein to regulate/reduce the subject's food intake and/or food cravings.

In a preferred embodiment, the invention provides a method for treating anxiety disorders, impulse control disorders, OCD, and/or anger/violence-related disorders, or regulating food intake and/or food cravings, in a patient in need thereof, comprising administering to the patient a therapeutically effective amount of ibogaine, ibogaine derivative, or a pharmaceutically acceptable salt and/or solvate thereof, wherein the patient is not addicted to cocaine or an opiate, and further wherein the therapeutically effective amount provides average ibogaine serum levels of between about 50 to about 180 ng/ml. In some embodiments, the average ibogaine serum level provided by the dosage is less than about 50 ng/mL. In one embodiment, the therapeutically effective amount is between about 1 mg to about 4 mg per kg of body weight. In one embodiment, the therapeutically effective amount is between about 50 ng to about 100 µg per kg of body weight. In one embodiment, an anxiety disorder is treated. In one embodiment, OCD is treated. In one embodiment, an impulse control disorder is treated. On one embodiment, an anger-related disorder is treated. in one embodiment, a violence-related disorder is treated. In one embodiment, symptoms of anger are reduced or eliminated. In one embodiment, violent outbursts are reduced or eliminated. In one embodiment, food intake is regulated. In one embodiment, food cravings are attenuated. In one embodiment, the ibogaine, ibogaine derivative, or pharmaceutically acceptable salt and/or solvate thereof is administered by sublingual, buccal, intranasal, or intrapulmonary delivery.

Dosage and Routes of Administration

In some embodiments, the composition is administered via sublingual, intranasal, buccal, or intrapulmonary delivery. In one aspect, the invention provides administering a pharmaceutical composition comprising a pharmaceutically effective amount of ibogaine and a pharmaceutically acceptable excipient, wherein the therapeutically effective amount of ibogaine is an amount that delivers an aggregate amount of ibogaine of about 50 ng to about 100 µg per kg body weight per day. In some aspects, the therapeutically effective amount of ibogaine is an amount that delivers an aggregate amount of ibogaine of about 50 ng to about 50 µg per kg body weight per day. In some aspects, the therapeutically effective amount of ibogaine is an amount that delivers an aggregate amount of ibogaine of about 50 ng to about 10 µg per kg body weight per day. In some aspects, the therapeutically effective amount of ibogaine is an amount that delivers an aggregate amount of ibogaine of about 50 ng to about 1 µg per kg body weight per day. In some aspects, the composition is administered once per day. In some aspects, the composition is administered two or more times per day. In some embodiments, the composition is administered less than once a day, for example once every two days, once every three days, once every four days, once a week, etc.

In some embodiments, the composition is administered via oral, buccal, transdermal, internal, pulmonary, rectal, nasal, vaginal, lingual, intravenous, intraarterial, intramuscular, intraperitoneal, intracutaneous or subcutaneous delivery.

In one embodiment, the dosage or aggregate dosage of compound is from about 1 mg to about 4 mg per kg body weight per day. The aggregate dosage is the combined dosage, for example the total amount of ibogaine, ibogaine derivative, or pharmaceutically acceptable salt and/or solvate thereof administered over a 24-hour period where smaller amounts are administered more than once per day.

In one embodiment, the dosage or aggregate dosage of ibogaine, ibogaine derivative, or salt or solvate thereof is from about 1 mg/kg to about 4 mg/kg body weight per day. The aggregate dosage is the combined dosage, for example the total amount of ibogaine, ibogaine derivative, or pharmaceutically acceptable salt or solvate thereof administered over a 24-hour period where smaller amounts are administered more than once per day. In one embodiment, the dosage or aggregate dosage of ibogaine, ibogaine derivative, or salt or solvate thereof is from about 1.3 mg/kg to about 4 mg/kg body weight. In one embodiment, the dosage or aggregate dosage of ibogaine, ibogaine derivative, or salt or solvate thereof is from about 1.3 mg/kg to about 3 mg/kg body weight. In one embodiment, the dosage or aggregate dosage of ibogaine, ibogaine derivative, or salt or solvate thereof is from about 1.3 mg/kg to about 2 mg/kg body weight. In one embodiment, the dosage or aggregate dosage of ibogaine, ibogaine derivative, or salt or solvate thereof is from about 1.5 mg/kg to about 3 mg/kg body weight. In one embodiment, the dosage or aggregate dosage of ibogaine, ibogaine derivative, or salt or solvate thereof is from about 1.7 mg/kg to about 3 mg/kg body weight. In one embodiment, the dosage or aggregate dosage of ibogaine, ibogaine derivative, or salt or solvate thereof is from about 2 mg/kg to about 4 mg/kg body weight. In one embodiment, the dosage or aggregate dosage of ibogaine, ibogaine derivative, or salt or solvate thereof is from about 2 mg/kg to about 3 mg/kg body weight. In one embodiment, the dosage or aggregate dosage of ibogaine, ibogaine derivative, or salt or solvate thereof is about 2 mg/kg body weight. The ranges include both extremes as well as any subrange or subvalue there between.

In one embodiment, the dosage or aggregate dosage of ibogaine, ibogaine derivative, or salt or solvate thereof is about 4 mg/kg body weight per day. In one embodiment, the dosage or aggregate dosage of ibogaine, ibogaine derivative, or salt or solvate thereof is about 3 mg/kg body weight per day. In one embodiment, the dosage or aggregate dosage of ibogaine, ibogaine derivative, or salt or solvate thereof is about 2 mg/kg body weight per day. In one embodiment, the dosage or aggregate dosage of ibogaine, ibogaine derivative, or salt or solvate thereof is about 1.9 mg/kg body weight per day. In one embodiment, the dosage or aggregate dosage of ibogaine, ibogaine derivative, or salt or solvate thereof is about 1.8 mg/kg body weight per day. In one embodiment, the dosage or aggregate dosage of ibogaine, ibogaine derivative, or salt or solvate thereof is about 1.7 mg/kg body weight per day. In one embodiment, the dosage or aggregate dosage of ibogaine, ibogaine derivative, or salt or solvate thereof is about 1.6 mg/kg body weight per day. In one embodiment, the dosage or aggregate dosage of ibogaine, ibogaine derivative, or salt or solvate thereof is about 1.5 mg/kg body weight per day. In one embodiment, the dosage or aggregate dosage of ibogaine, ibogaine derivative, or salt or solvate thereof is about 1.4 mg/kg body weight per day. In one embodiment, the dosage or aggregate dosage of ibogaine, ibogaine derivative, or salt or solvate thereof is about 1.3 mg/kg body weight per day. In one embodiment, the dosage or aggregate dosage of ibogaine, ibogaine derivative, or salt or solvate thereof is about 1.2 mg/kg body weight per day. In one embodiment, the dosage or aggregate dosage of ibogaine, ibogaine derivative, or salt or solvate thereof is about 1.1 mg/kg body weight per day. In one embodiment, the dosage or aggregate dosage of ibogaine, ibogaine derivative, or salt or solvate thereof is about 1 mg/kg body weight per day.

In one embodiment, the dosage or aggregate dosage of ibogaine, ibogaine derivative, or salt or solvate thereof is between about 70 mg and about 150 mg. In one embodiment, the dosage or aggregate dosage of ibogaine, ibogaine derivative, or salt or solvate thereof is between about 75 mg and about 150 mg. In one embodiment, the dosage or aggregate dosage of ibogaine, ibogaine derivative, or salt or solvate thereof is between about 80 mg and about 140 mg. In one embodiment, the dosage or aggregate dosage of ibogaine, ibogaine derivative, or salt or solvate thereof is between about 90 mg and about 140 mg. In one embodiment, the dosage or aggregate dosage of ibogaine, ibogaine derivative, or salt or solvate thereof is between about 90 mg and about 130 mg. In one embodiment, the dosage or aggregate dosage of ibogaine, ibogaine derivative, or salt or solvate thereof is between about 100 mg and about 130 mg. In one embodiment, the dosage or aggregate dosage of ibogaine, ibogaine derivative, or salt or solvate thereof is between about 110 mg and about 130 mg. The ranges include both extremes as well as any subrange or subvalue there between.

In one embodiment, the average serum concentration of ibogaine is from about 50 ng/mL to about 180 ng/mL, or about 60 ng/mL to about 180 ng/mL. In one embodiment, the average serum concentration of ibogaine is from about 50 ng/mL to about 150 ng/mL, or about 60 ng/mL to about 150 ng/mL. In one embodiment, the average serum concentration of ibogaine is from about 50 ng/mL to about 100 ng/mL, or about 60 ng/mL to about 100 ng/mL. In one embodiment, the average serum concentration of ibogaine is from about 80 ng/mL to about 150 ng/mL. In one embodiment, the average serum concentration of ibogaine is from about 80 ng/mL to about 100 ng/mL. The ranges include both extremes as well as any subrange or subvalue there between.

In one embodiment, the dosage of ibogaine, ibogaine derivative, or pharmaceutically acceptable salt or solvate thereof provides a serum concentration of between about 1000 ng*hr/mL and about 6000 ng*hr/mL. In one embodiment, the dosage of ibogaine, ibogaine derivative, or pharmaceutically acceptable salt or solvate thereof provides a serum concentration of between about 1200 ng*hr/mL and about 5800 ng*hr/mL. In one embodiment, the dosage of ibogaine, ibogaine derivative, or pharmaceutically acceptable salt or solvate thereof provides a serum concentration of between about 1200 ng*hr/mL and about 5500 ng*hr/mL. The ranges include both extremes as well as any subrange or subvalue there between.

In one embodiment, the dosage of ibogaine, ibogaine derivative, or pharmaceutically acceptable salt or solvate thereof provides a maximum serum concentration (Cmax) of less than about 250 ng/mL. In one embodiment, the dosage of ibogaine, ibogaine derivative, or pharmaceutically acceptable salt or solvate thereof provides a Cmax between about 40 ng/mL and about 250 ng/mL. In a preferred embodiment, the dosage of ibogaine, ibogaine derivative, or pharmaceutically acceptable salt or solvate thereof provides a Cmax between about 60 ng/mL and about 200 ng/mL. In one embodiment, the dosage of ibogaine, ibogaine derivative, or pharmaceutically acceptable salt or solvate thereof provides a Cmax between about 100 ng/mL and about 180 ng/mL. The ranges include both extremes as well as any subrange or subvalue there between.

In one embodiment, ibogaine is administered at an amount by weight that is twice that administered for noribogaine for treating a same or similar condition. For example, and without limitation, an administration of a dose 80 mg ibogaine approximates a dose of 40 mg noribogaine.

In some embodiments, the patient is administered periodically, such as once, twice, three time, four times or five time daily with ibogaine, ibogaine derivative, or salt and/or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made by a qualified clinician.

In another embodiment, there is provided a unit dose of ibogaine, ibogaine derivative, or salt or solvate thereof which is about 50 mg to about 200 mg per dose. In one embodiment, the unit dose is about 50 to about 120 mg per dose. In one embodiment, the unit dose is about 120 mg per dose. It being understood that the term "unit dose" means a dose sufficient to provide therapeutic results whether given all at once or serially over a period of time.

In some embodiments, the patient is administered an initial dose of ibogaine, ibogaine derivative, or pharmaceutically acceptable salt or solvate thereof, followed by one or more additional doses. In one embodiment, such a dosing regimen provides an average serum concentration of ibogaine of about 50 ng/mL to about 180 ng/mL. In one embodiment, the one or more additional doses maintain an average serum concentration of about 50 ng/mL to about 180 ng/mL over a period of time.

In some embodiments, the initial dose of ibogaine, ibogaine derivative, or salt or solvate thereof is from about 75 mg to about 120 mg. In one embodiment, the initial dose is about 75 mg. In one embodiment, the initial dose is about 80 mg. In one embodiment, the initial dose is about 85 mg. In one embodiment, the initial dose is about 90 mg. In one embodiment, the initial dose is about 95 mg. In one embodiment, the initial dose is about 100 mg. In one embodiment, the initial dose is about 105 mg. In one embodiment, the initial dose is about 110 mg. In one embodiment, the initial dose is about 115 mg. In one embodiment, the initial dose is about 120 mg.

In some embodiments, the one or more additional doses are lower than the initial dose. In one embodiment, the one or more additional doses are from about 5 mg to about 50 mg. In one embodiment, the one or more additional doses may or may not comprise the same amount of ibogaine, ibogaine derivative, or salt or solvate thereof. In one embodiment, at least one additional dose is about 5 mg. In one embodiment, at least one additional dose is about 10 mg. In one embodiment, at least one additional dose is about 15 mg. In one embodiment, at least one additional dose is about 20 mg. In one embodiment, at least one additional dose is about 25 mg. In one embodiment, at least one additional dose is about 30 mg. In one embodiment, at least one additional dose is about 35 mg. In one embodiment, at least one additional dose is about 40 mg. In one embodiment, at least one additional dose is about 45 mg. In one embodiment, at least one additional dose is about 50 mg.

In one embodiment, the one or more additional doses are administered periodically. In one embodiment, the one or more additional doses are administered approximately every 4 hours. In one embodiment, the one or more additional doses are administered every 6 hours. In one embodiment, the one or more additional doses are administered approximately every 8 hours. In one embodiment, the one or more additional doses are administered approximately every 10 hours. In one embodiment, the one or more additional doses are administered approximately every 12 hours. In one embodiment, the one or more additional doses are administered approximately every 18 hours. In one embodiment, the one or more additional doses are administered approximately every 24 hours. In one embodiment, the one or more additional doses are administered approximately every 36 hours. In one embodiment, the one or more additional doses are administered approximately every 48 hours.

In one aspect, this invention relates to a method for attenuating symptoms of anxiety disorder, impulse control disorder, or an anger and/or violence-related disorder in a human patient, comprising administering to the patient a dosage of ibogaine or pharmaceutically acceptable salt and/or solvate thereof that provides an average serum concentration of about 50 ng/mL to about 180 ng/mL, said concentration being sufficient to attenuate said symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment.

In one aspect, this invention relates to a method for attenuating food cravings in a human patient, comprising administering to the patient a dosage of ibogaine or pharmaceutically acceptable salt and/or solvate thereof that provides an average serum concentration of about 50 ng/mL to about 250 ng/mL, said concentration being sufficient to attenuate said cravings while maintaining a QT interval of less than about 500 ms during said treatment. In some embodiments, the concentration is sufficient to attenuate said cravings while maintaining a QT interval of less than about 470 ms during treatment. Preferably, the concentration is sufficient to attenuate said cravings while maintaining a QT interval of less than about 450 ms during treatment. In one embodiment, the concentration is sufficient to attenuate said cravings while maintaining a QT interval of less than about 420 ms during treatment.

In one embodiment, the QT interval is not prolonged more than about 50 ms. In one embodiment, the QT interval is not prolonged more than about 40 ms. In one embodiment, the QT interval is not prolonged more than about 30 ms. In a preferred embodiment, the QT interval is not prolonged more than about 20 ms. In one embodiment, the QT interval is not prolonged more than about 10 ms.

The compositions, provided herein or known, suitable for administration in accordance with the methods provide herein, can be suitable for a variety of delivery modes including, without limitation, oral and transdermal delivery. Compositions suitable for internal, pulmonary, rectal, nasal, vaginal, lingual, intravenous, intraarterial, intramuscular, intraperitoneal, intracutaneous and subcutaneous routes may also be used. A particularly suitable composition comprises a composition suitable for a transdermal route of delivery in which the ibogaine or ibogaine derivative is applied as part of a cream, gel or, preferably, patch (for examples of transdermal formulations, see U.S. Pat. Nos. 4,806,341; 5,149,538; and 4,626,539, each of which are incorporated herein by reference). Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

Ibogaine, an ibogaine derivative, or a pharmaceutically acceptable salt and/or solvate thereof can also be used in conjunction with any of the vehicles and excipients commonly employed in pharmaceutical preparations, e.g., talc, gum Arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing ibogaine may be prepared using conventional techniques that may include sterile isotonic saline, water, 1,3-butanediol, ethanol, 1,2-propylene glycol, polyglycols mixed with water, Ringer's solution, etc.

Patient Pre-screening and Monitoring

Pre-screening of patients before treatment with ibogaine and/or monitoring of patients during ibogaine treatment may be required to ensure that QT interval is not prolonged beyond a certain value. For example, QT interval greater than about 500 ms can be considered dangerous for individual patients. Pre-screening and/or monitoring may be necessary at high levels of ibogaine treatment.

In one embodiment, a patient receiving a therapeutic dose of ibogaine is monitored in a clinical setting. Monitoring may be necessary to ensure the QT interval is not prolonged to an unacceptable degree. A "clinical setting" refers to an inpatient setting (e.g., inpatient clinic, hospital, or other facility) or an outpatient setting with frequent, regular monitoring (e.g., outpatient clinic that is visited daily or frequently). Monitoring includes monitoring of QT interval. Methods for monitoring of QT interval are well-known in the art, for example by ECG.

In a preferred embodiment, the patient receiving treatment with ibogaine or derivative thereof is not monitored in a clinical setting. In one embodiment, the patient is monitored periodically, for example daily, weekly, monthly, or occasionally.

In one aspect, this invention relates to a method for treating an anxiety disorder, an impulse control disorder, or an anger/violence-related disorder, and/or treating or attenuating the symptoms thereof in a patient, comprising selecting a patient exhibiting symptoms of an anxiety disorder, impulse control disorder, or anger/violence-related disorder who is prescreened to evaluate the patient's expected tolerance for prolongation of QT interval, administering to the patient a dosage of ibogaine, ibogaine derivative, or pharmaceutically acceptable salt and/or solvate thereof that provides an average serum concentration of about 50 ng/mL to about 400 ng/mL, said concentration being sufficient to inhibit or ameliorate said disorder or symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment.

In one aspect, this invention relates to a method for regulating food intake, and/or treating or attenuating food cravings, in a patient, comprising selecting an overweight or obese patient who is prescreened to evaluate the patient's expected tolerance for prolongation of QT interval, administering to the patient a dosage of ibogaine, ibogaine derivative, or pharmaceutically acceptable salt and/or solvate thereof that provides an average serum concentration of about 50 ng/mL to about 180 ng/mL, said concentration being sufficient to inhibit or ameliorate said disorder or symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment.

In some embodiments, the method comprises prescreening the patient. In one embodiment, prescreening of the patient comprises ascertaining that ibogaine treatment will not result in a QT interval over about 500 ms. In one embodiment, prescreening of the patient comprises ascertaining that ibogaine treatment will not result in a QT interval over about 470 ms. In one embodiment, prescreening comprises ascertaining that ibogaine treatment will not result in a QT interval over about 450 ms. In one embodiment, prescreening comprises ascertaining that ibogaine treatment will not result in a QT interval over about 420 ms. In one embodiment, prescreening comprises determining the patient's pre-treatment QT interval.

As it relates to pre-screening or pre-selection of patients, patients may be selected based on any criteria as determined by the skilled clinician. Such criteria may include, by way of non-limiting example, pre-treatment QT interval, pre-existing cardiac conditions, risk of cardiac conditions, age, sex, general health, and the like. The following are examples of selection criteria for disallowing ibogaine treatment or restricting dose of ibogaine administered to the patient: high QT interval before treatment (e.g., such that there is a risk of the patient's QT interval exceeding 500 ms during treatment); congenital long QT syndrome; bradycardia; hypokalemia or hypomagnesemia; recent acute myocardial infarction; uncompensated heart failure; and taking other drugs that increase QT interval. In some embodiments, the methods can include selecting and/or administering/providing ibogaine to a patient that lacks one more of such criteria.

In one embodiment, this invention relates to pre-screening a patient to determine if the patient is at risk for prolongation of the QT interval beyond a safe level. In one embodiment, a patient at risk for prolongation of the QT interval beyond a safe level is not administered ibogaine. In one embodiment, a patient at risk for prolongation of the QT interval beyond a safe level is administered ibogaine at a limited dosage.

In one embodiment, this invention relates to monitoring a patient who is administered a therapeutic dose of ibogaine. In one embodiment, the dose of ibogaine is reduced if the patient has serious adverse side effects. In one embodiment, the ibogaine treatment is discontinued if the patient has serious adverse side effects. In one embodiment, the adverse side effect is a QT interval that is prolonged beyond a safe level. The determination of a safe level of prolongation is within the skill of a qualified clinician.

EXAMPLES

Example 1. Social Interaction Test (SIT)

Animals: Male albino Sprague-Dawley rats (Taconic Farms, N.Y.) are housed in pairs under a 12 hr light dark cycle (lights on at 0700 hrs.) with free access to food and water.

Rats are allowed to acclimate to the animal care facility for 5 days and are housed singly for 5 days prior to testing. Animals are handled for 5 minutes per day. On the test day, weight matched pairs of rats (±5%), unfamiliar to each other, are given identical treatments and returned to their home cages. Animals are randomly divided into 5 treatment groups, with 5 pairs per group, and are given one of the following i.p. treatments: Test Compound (1, 2 or 4 mg/kg), vehicle (1 ml/kg) or chlordiazepoxide (5 mg/kg). Dosing is done 1 hour prior to testing. Rats are subsequently placed in a white perspex test box or arena (54×37×26 cm), whose floor is divided up into 24 equal squares, for 15 minutes. An air conditioner is used to generate background noise and to keep the room at approximately 74° F. All sessions are videotaped using a JVC camcorder (model GR-SZ1, Elmwood Park, N.J.) with either TDK (HG ultimate brand) or Sony 30 minute videocassettes. All sessions are conducted between 13:00 and 16:30 hours. Active social interaction, defined as grooming, sniffing, biting, boxing, wrestling, following and crawling over or under, is scored using a stopwatch (Sportsline model no. 226, 1/100 sec. discriminability). The number of episodes of rearing (animal completely raises up its body on its hind limbs), grooming (licking, biting, scratching of body), and face ishing (i.e. hands are moved repeatedly over face), and number of squares crossed are scored. Passive social interaction (animals are lying beside or on top of each other) is not scored. All behaviors are assessed later by an observer who is blind as to the treatment of each pair. At the end of each test, the box is thoroughly wiped with moistened paper towels.

Data Analysis: The social interaction data (time interacting, rearing and squares crossed) are subjected to a randomized, one-way ANOVA and post hoc tests conducted using the Student-Newman-Keuls test. The data are subjected to a test of normality (Shapiro-Wilk test). The data are analyzed using the GBSTAT program, version 6.5 (Dynamics Microsystems, Inc., Silver Spring, Md., 1997).

Example 2. Efficacy of Ibogaine, Ibogaine Derivative, or a Pharmaceutically Acceptable Salt Thereof on Anxiety-Related Disorders in Humans The efficacy of ibogaine, ibogaine derivative, or a pharmaceutically acceptable salt thereof is evaluated in participants undergoing treatment for an anxiety-related disorder in a randomized, placebo-controlled, double-blind trial. Patients are not taking any other medications to treat anxiety. Patients are administered placebo or 60 mg or 120 mg of the compound and QT interval is measured.

Example 3. Efficacy of Ibogaine, Ibogaine Derivative, or a Pharmaceutically Acceptable Salt Thereof on Impulse Control Disorders in Humans The efficacy of ibogaine, ibogaine derivative, or a pharmaceutically acceptable salt thereof is evaluated in participants undergoing treatment for an impulse control disorder in a randomized, placebo-controlled, double-blind trial. Patients are not taking any other medications to treat anxiety. Patients are administered placebo or 60 mg or 120 mg of the compound and QT interval is measured.

Example 4. Efficacy of Ibogaine, Ibogaine Derivative, or a Pharmaceutically Acceptable Salt Thereof on Violence-Related Disorders in Humans The efficacy of ibogaine, ibogaine derivative, or a pharmaceutically acceptable salt thereof is evaluated in participants undergoing treatment for a violence-related disorder in a randomized, placebo-controlled, double-blind trial. Patients are not taking any other medications to treat anxiety. Patients are administered placebo or 60 mg or 120 mg of the compound and QT interval is measured. Mean prolongation of the QT interval and/or the severity of violent outbursts, are determined by self-evaluation and clinical evaluation.

Example 5. Efficacy of Ibogaine, Ibogaine Derivative, or a Pharmaceutically Acceptable Salt Thereof on Food Intake in Humans The efficacy of ibogaine, ibogaine derivative, or a pharmaceutically acceptable salt thereof is evaluated in participants undergoing treatment for obesity related to over-eating in a randomized, placebo-controlled, double-blind trial. Patients are not taking any other medications to treat anxiety. Patients are administered placebo or 60 mg or 120 mg of the compound and QT interval is measured. Mean prolongation of the QT interval, weight loss and food intake and/or cravings, are determined by self-evaluation and clinical evaluation.

What is claimed is:

1. A method for treating an impulse control disorder in a patient in need thereof, comprising administering to the patient a therapeutically effective amount of a compound selected from ibogaine, an ibogaine derivative, and a pharmaceutically acceptable salt and/or solvate thereof, the ibogaine derivative selected from the group consisting of coronaridine, voacangine, 18-methoxycoronaridine, 2-methoxyethyl-18-methoxycoronaridinate, and 18-methylaminocoronaridine: wherein the patient is not addicted to cocaine or an opiate, and further wherein the therapeutically effective amount provides an efficacious average serum level of ibogaine or the ibogaine derivative of less than about 180 ng/mL while maintaining a QT interval of less than about 500 ms during said treatment.

2. The method of claim 1, wherein the impulse control disorder is selected from the group consisting of borderline personality disorder, conduct disorder, antisocial personality disorder, attention deficit hyperactivity disorder, attention deficit disorder, schizophrenia, mood disorders, pathological gambling, pyromania, intermittent explosive disorder, kleptomania, sexual compulsion, paraphilia, Internet addiction, trichotillomania, pathological skin picking, and compulsive shopping.

3. A method of claim 1, comprising:
   a) administering an initial dose of ibogaine, the ibogaine derivative, or the pharmaceutically, acceptable salt or solvate thereof, wherein the initial dose provides an average serum concentration of less than about 180 ng/mL; and
   b) administering at least one additional dose of ibogaine, the ibogaine derivative, or the pharmaceutically acceptable salt or solvate thereof, such that the at least one additional dose maintains the average serum concentration of less than about 180 ng/mL for a period of time.

4. The method of claim 3, wherein the initial dose is from about 75 mg to about 120 mg.

5. The method of claim 3, wherein the at least one additional dose is from about 5 mg to about 25 mg.

6. The method of claim 3, wherein the at least one additional dose is administered from about 6 hours to about 24 hours after the initial dose.

7. The method of claim 3, wherein at least two additional doses are administered, and further wherein the additional doses are administered from about 6 hours to about 24 hours after the previous dose.

8. The method of claim 1, wherein the QT interval is less than about 450 ms.

9. The method of claim 1, further comprising selecting a patient who is prescreened to evaluate tolerance for prolongation of QT interval.

10. The method of claim 1, wherein the ibogaine, the ibogaine derivative, or the pharmaceutically acceptable salt or solvate thereof is administered by sublingual, buccal, intranasal, or intrapulmonary delivery.

11. The method of claim 1, wherein ibogaine or a pharmaceutically acceptable salt or solvate thereof is administered.

12. The method of claim 1, wherein the ibogaine derivative or a pharmaceutically acceptable salt or solvate thereof is administered.

13. The method of claim 1, wherein the efficacious average serum level of ibogaine or the ibogaine derivative provided is less than about 50 ng/mL.

14. The method of claim 1, wherein the efficacious average serum level of ibogaine or the ibogaine derivative provided is between about 50 ng/mL and about 180 ng/mL.

* * * * *

UNITED STATES PATENT AND TRADEMARK OFFICE
CERTIFICATE OF CORRECTION

PATENT NO. : 11,077,118 B2
APPLICATION NO. : 15/454305
DATED : August 3, 2021
INVENTOR(S) : Maillet It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twenty-fourth Day of January, 2023

Katherine Kelly Vidal
*Director of the United States Patent and Trademark Office*